US012048661B2

(12) United States Patent
Upchurch et al.

(10) Patent No.: US 12,048,661 B2
(45) Date of Patent: *Jul. 30, 2024

(54) PATIENT TRANSPORT APPARATUS WITH ELECTRO-MECHANICAL BRAKING SYSTEM

(71) Applicant: Stryker Corporation, Kalamazoo, MI (US)

(72) Inventors: Joseph Adam Upchurch, Houston, TX (US); Tyler Ethen, Portage, MI (US); Gary L. Bartley, Kalamazoo, MI (US); William Dwight Childs, Plainwell, MI (US); Ryan Ross, New Carlisle, IN (US)

(73) Assignee: Stryker Corporation, Kalamazoo, MI (US)

( * ) Notice: Subject to any disclaimer, the term of this patent is extended or adjusted under 35 U.S.C. 154(b) by 988 days.

This patent is subject to a terminal disclaimer.

(21) Appl. No.: 17/022,825

(22) Filed: Sep. 16, 2020

(65) Prior Publication Data

US 2020/0405555 A1 Dec. 31, 2020

Related U.S. Application Data

(63) Continuation of application No. 16/210,876, filed on Dec. 5, 2018, now Pat. No. 10,806,653.
(Continued)

(51) Int. Cl.
*A61G 7/05* (2006.01)
*A61G 1/02* (2006.01)
(Continued)

(52) U.S. Cl.
CPC .......... *A61G 7/0528* (2016.11); *A61G 1/0287* (2013.01); *A61G 7/018* (2013.01);
(Continued)

(58) Field of Classification Search
CPC ........ A61G 7/018; A61G 7/08; A61G 7/0506; A61G 7/0528; A61G 7/1013;
(Continued)

(56) References Cited

U.S. PATENT DOCUMENTS 4,667,365 A 5/1987 Martinek
5,133,106 A 7/1992 Milbredt et al.
(Continued)

FOREIGN PATENT DOCUMENTS

EP 1782515 B1 10/2012
EP 3543035 B1 * 5/2023 ............. B60B 19/00
(Continued)

OTHER PUBLICATIONS

English language abstract and machine-assisted English translation for EP 1 782 515 extracted from espacenet.com database on Dec. 9, 2019, 6 pages.
(Continued)

*Primary Examiner* — David R Hare
(74) *Attorney, Agent, or Firm* — Howard & Howard Attorneys PLLC

(57) ABSTRACT

A patient transport apparatus comprises a base, a patient support deck, a wheel assembly, and a braking system. The wheel assembly includes a wheel and a braking mechanism. The braking system includes a linkage assembly, a manual actuator, and an electrical braking assembly. The linkage assembly is arranged to place the braking mechanism in a braked state and a released state. The manual actuator moves the linkage assembly manually to place the braking mechanism in the braked state and the released state. The electrical braking assembly includes a driving assembly that moves to a first position and to a second positing that causes the linkage assembly to place the braking mechanism in the braked state and the released state. The linkage assembly is (Continued)

movable relative to the driving assembly to enable the braking mechanism to be manually actuated with the manual actuator.

20 Claims, 18 Drawing Sheets

Related U.S. Application Data

(60) Provisional application No. 62/609,025, filed on Dec. 21, 2017.

(51) Int. Cl.
*A61G 7/018* (2006.01)
*A61G 7/08* (2006.01)
*A61G 7/10* (2006.01)

(52) U.S. Cl.
CPC ........ *A61G 7/08* (2013.01); *A61B 2562/0252* (2013.01); *A61G 7/1046* (2013.01); *A61G 7/1067* (2013.01); *A61G 2203/30* (2013.01); *A61G 2203/32* (2013.01)

(58) Field of Classification Search
CPC ................ A61G 7/1046; A61G 7/1067; A61G 2203/30; A61G 2203/32; A61G 1/0287; A61B 2562/0252; A61B 5/6892; B60B 33/0078; B60B 33/0081; B60B 33/0092; B60B 33/021; B60B 33/028; B60B 33/026
USPC .......................................................... 5/613
See application file for complete search history.

(56) References Cited

U.S. PATENT DOCUMENTS

| | | |
|---|---|---|
| 5,244,062 A | 9/1993 | Felton |
| 5,450,639 A | 9/1995 | Weismiller et al. |
| 6,321,878 B1 | 11/2001 | Mobley et al. |
| 6,584,641 B1 | 7/2003 | Milbredt |
| 6,865,775 B2 | 3/2005 | Ganance |
| 6,877,572 B2 | 4/2005 | Vogel et al. |
| 7,159,695 B2 | 1/2007 | Strong |
| 7,195,253 B2 | 3/2007 | Vogel et al. |
| 7,200,894 B2 | 4/2007 | Block et al. |
| 7,273,115 B2 | 9/2007 | Kummer et al. |
| 7,302,717 B2 | 12/2007 | Reinke et al. |
| 7,346,942 B2 | 3/2008 | Reinke et al. |
| 7,406,745 B1 | 8/2008 | Chou |
| 7,407,024 B2 | 8/2008 | Vogel et al. |
| 7,480,948 B2 | 1/2009 | Reinke et al. |
| 7,698,760 B2 | 4/2010 | Reckelhoff et al. |
| 7,810,822 B2 | 10/2010 | Figel et al. |
| 7,828,092 B2 | 11/2010 | Vogel et al. |
| 7,950,108 B2 | 5/2011 | Yang et al. |
| 8,016,301 B2 | 9/2011 | Figel et al. |
| 8,024,101 B2 | 9/2011 | Froli |
| 8,051,533 B2 | 11/2011 | Block et al. |
| 8,205,297 B2 | 6/2012 | Fallshaw et al. |
| 8,267,206 B2 | 9/2012 | Vogel et al. |
| 8,341,777 B2 | 1/2013 | Hensley et al. |
| 8,452,508 B2 | 5/2013 | Frolik et al. |
| 8,484,802 B1 | 7/2013 | Lin et al. |
| 8,516,656 B2 | 8/2013 | Lin et al. |
| 8,528,704 B2 | 9/2013 | Hayes et al. |
| 8,590,074 B2 | 11/2013 | Hornbach et al. |
| 8,640,832 B2 | 2/2014 | Chen et al. |
| 8,701,229 B2 | 4/2014 | Lemire et al. |
| 8,776,314 B2 | 7/2014 | Hofrichter et al. |
| 9,173,795 B2 | 11/2015 | Heidlage et al. |
| 9,333,801 B2 | 5/2016 | Chen et al. |
| 9,498,397 B2 | 11/2016 | Hight et al. |
| 9,555,778 B2 | 1/2017 | Lemire et al. |
| 10,052,249 B2 | 8/2018 | Elliott et al. |
| 10,437,348 B2 | 10/2019 | Hayes et al. |
| 10,568,792 B2 | 2/2020 | Derenne et al. |
| 10,806,653 B2 * | 10/2020 | Upchurch ............... A61G 7/018 |
| 10,905,612 B2 * | 2/2021 | Derenne .................. A61G 7/08 |
| 11,039,964 B2 * | 6/2021 | Paul ...................... A61G 1/0237 |
| 2001/0011393 A1 | 8/2001 | Brooke et al. |
| 2002/0174515 A1 | 11/2002 | Strong |
| 2004/0117943 A1 | 6/2004 | Block et al. |
| 2004/0181875 A1 | 9/2004 | Shiery et al. |
| 2008/0289108 A1 * | 11/2008 | Menkedick ............ A61G 7/052 5/610 |
| 2010/0138128 A1 | 6/2010 | Strothmann et al. |
| 2010/0175222 A1 * | 7/2010 | Fallshaw ............. B60B 33/0073 16/35 R |
| 2012/0298459 A1 | 11/2012 | Lubbers et al. |
| 2012/0316686 A1 | 12/2012 | Dueckman |
| 2013/0111664 A1 | 5/2013 | Childs et al. |
| 2014/0109342 A1 | 4/2014 | Hofrichter et al. |
| 2014/0238784 A1 | 8/2014 | Yeo |
| 2014/0324315 A1 | 10/2014 | Brondum |
| 2015/0266342 A1 | 9/2015 | Howard et al. |
| 2016/0297242 A1 | 10/2016 | Hein |
| 2017/0008340 A1 | 1/2017 | Iiyama et al. |
| 2017/0020752 A1 * | 1/2017 | Childs ..................... B60T 7/102 |
| 2017/0100962 A1 | 4/2017 | Kloss et al. |
| 2017/0172829 A1 | 6/2017 | Tessmer et al. |
| 2018/0168897 A1 | 6/2018 | Jonsson |
| 2019/0008708 A1 * | 1/2019 | Moreno ................ G06F 3/0489 |
| 2019/0192364 A1 | 6/2019 | Upchurch et al. |
| 2019/0350795 A1 | 11/2019 | Crombie et al. |
| 2022/0378635 A1 * | 12/2022 | Neihouser ............ A61G 7/0528 |

FOREIGN PATENT DOCUMENTS

| | | |
|---|---|---|
| WO | 2008148169 A1 | 12/2008 |
| WO | 2013071932 A1 | 5/2013 |

OTHER PUBLICATIONS

Del City, "Wire Loom Routing Clips Webpage", <https://www.delcity.net/store/Wire-Loom-Routing-Clips/p_800840.h_800841.r_IF1003?mkwid=s&crid=38094426869&mp_kw=&mp_mt=&gclid=EAlalQobChMI94qgma6R4QIVBA1pCh3H3AWqEAQYBSABEgKjvPD_BwE>, 2019, 1 page.

McMaster-Carr, Push-In Rivets with Ribbed Shank Webpage, https://www.mcmaster.com/90221a416, 2019, 1 page.

Stryker Medical, "Prime Series Stretcher Maintenance Manual", REF 1115, 111504090002 Rev. B.0, Dec. 2018, 472 pages.

* cited by examiner

PATIENT TRANSPORT APPARATUS WITH ELECTRO-MECHANICAL BRAKING SYSTEM

CROSS-REFERENCE TO RELATED APPLICATIONS

The subject patent application is a continuation of U.S. patent application Ser. No. 16/210,876 filed on Dec. 5, 2018 which, in turn, claims priority to and all the benefits of U.S. Provisional Patent Application No. 62/609,025 filed on Dec. 21, 2017, the disclosures of each of which are hereby incorporated by reference in their entirety.

BACKGROUND

Patient transport apparatuses, such as hospital beds, stretchers, cots, tables, wheelchairs, and chairs facilitate care of patients in a health care setting. Conventional patient transport apparatuses comprise a support structure having a patient support deck upon which the patient is supported, a wheel assembly to allow the patient transport apparatus to move along the floor, and a braking system that brakes the wheels to stop the movement of the patient transport apparatus.

At least some known braking systems include manual foot pedals located on the support structure under the patient support deck. There are certain disadvantages associated with such foot pedals. For example, during activation, a caregiver such as a nurse has to hold on to the support structure, balance on one foot and stretch the other foot under the patient support deck to engage or disengage a brake mechanism using the foot pedal. This can be difficult, especially if the nurse is attending to other needs of the patient. Electrical braking systems are known to simplify engagement and disengagement of the brake mechanism, but these electrical braking systems fail to be seamlessly integrated with a manual braking system so that the manual braking system and the electrical braking system can be selectively used for braking during normal operation without additional effort from the user.

A patient transport apparatus with a braking system is desired that addresses one or more of the aforementioned challenges.

DETAILED DESCRIPTION

Figure 1:
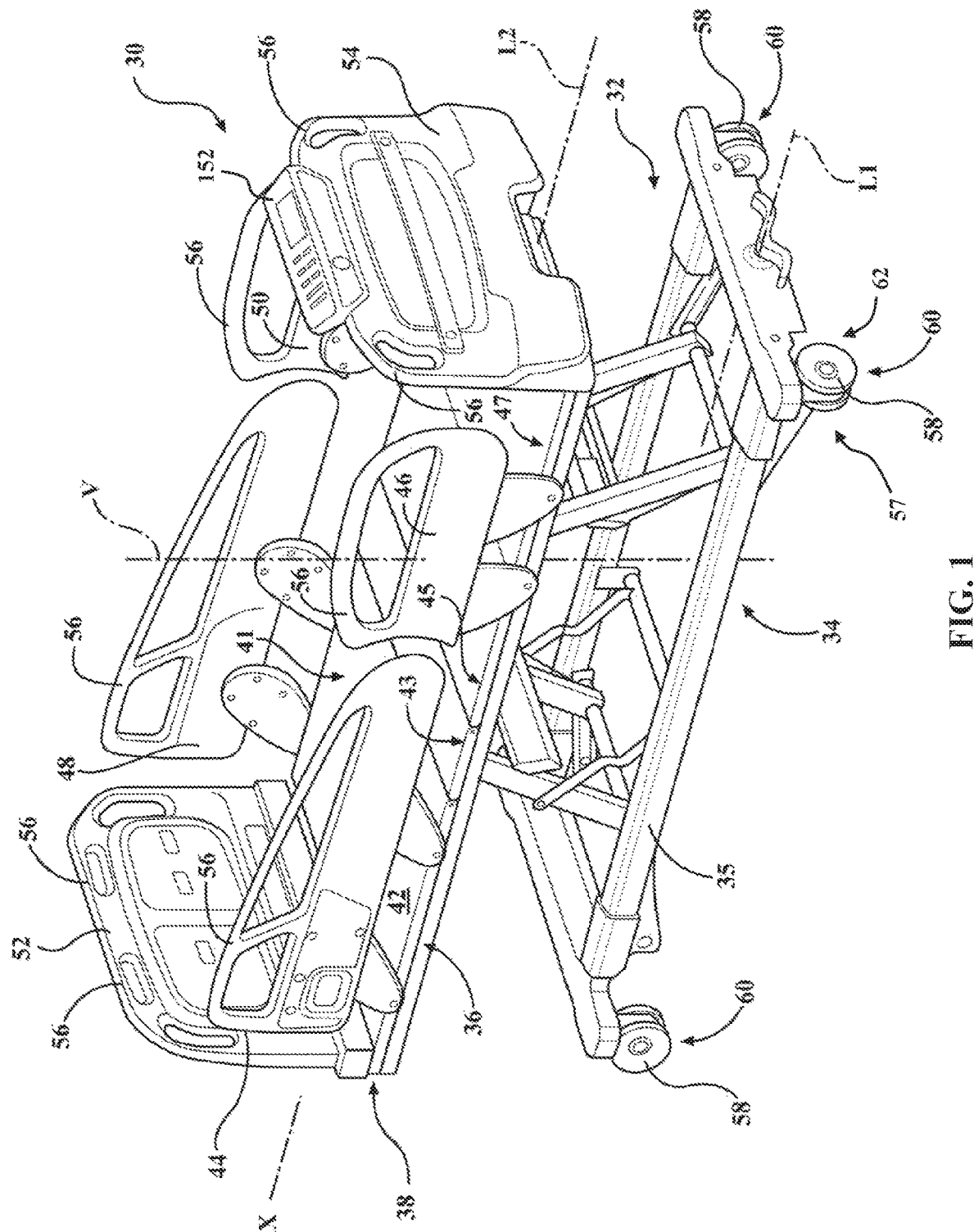
FIG. 1 is perspective view of a patient transport apparatus.
Figure 2:
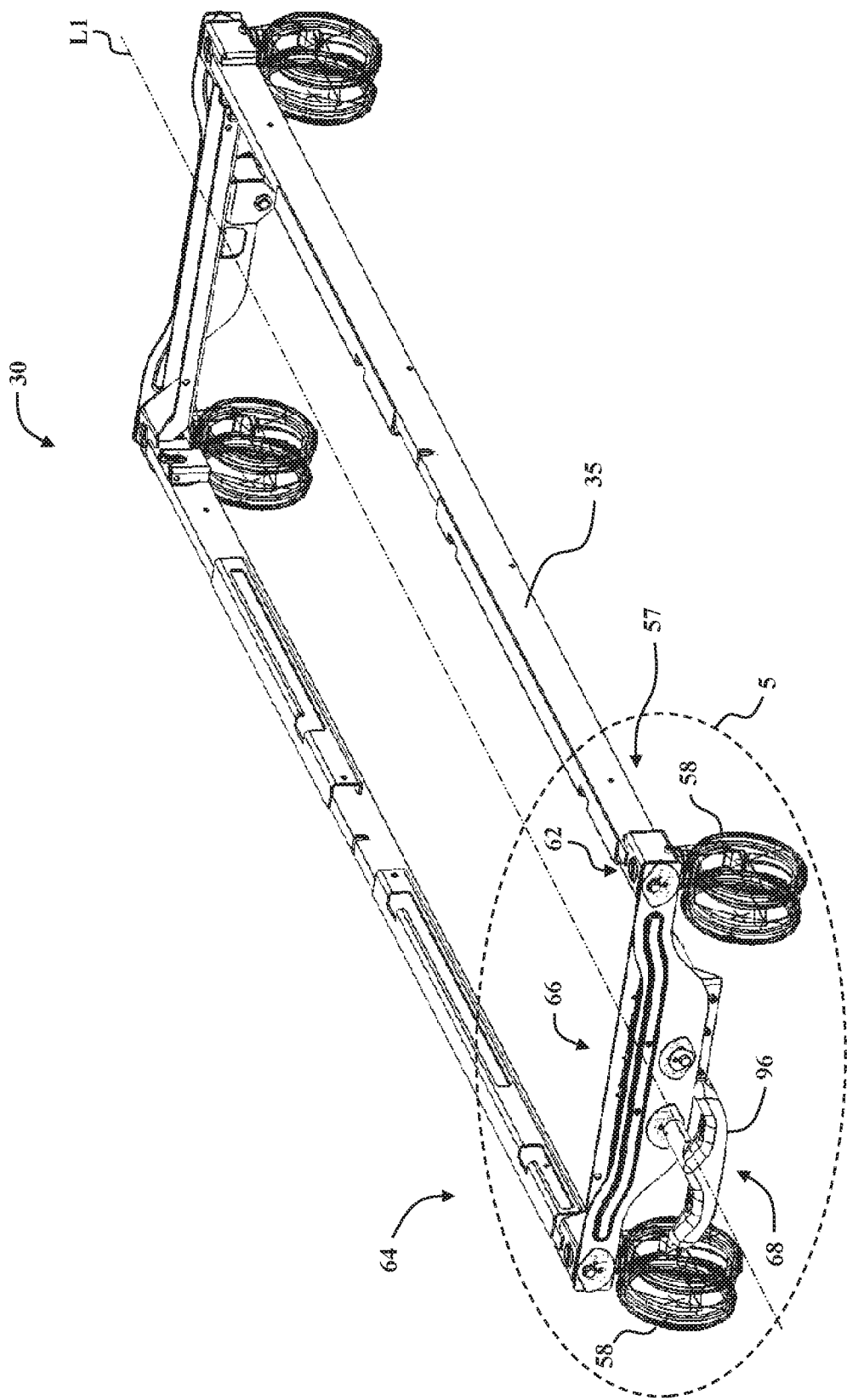
FIG. 2 is a perspective view of a portion of the patient transport apparatus illustrating an electro-mechanical braking system.
Figure 3:
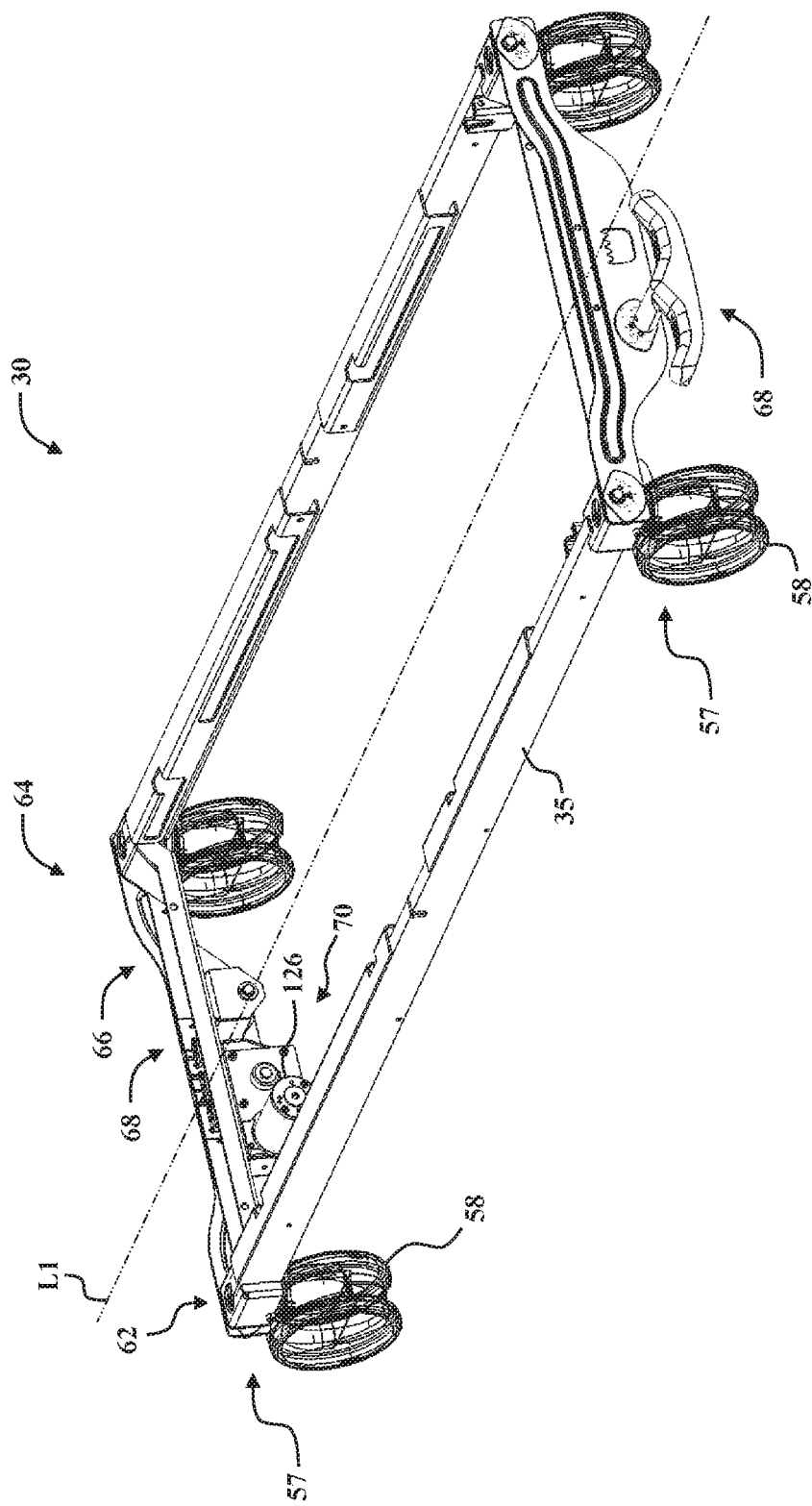
FIG. 3 is another perspective view of a portion of the patient transport apparatus illustrating the electro-mechanical braking system.

Referring to FIG. 1, a patient transport apparatus 30 is shown for supporting a patient in a health care setting. The patient transport apparatus 30 illustrated in FIG. 1 comprises a hospital bed. In other embodiments, however, the patient transport apparatus 30 may comprise a stretcher, cot, table, wheelchair, chair, or similar apparatus utilized in the care of a patient.

A support structure 32 provides support for the patient. The support structure 32 illustrated in FIG. 1 comprises a base 34 and a support frame 36. The base 34 comprises a base frame 35. The support frame 36 is spaced above the base frame 35 in FIG. 1. The support structure 32 also comprises a patient support deck 38 disposed on the support frame 36. The patient support deck 38 comprises several sections, some of which are capable of articulating (e.g., pivoting) relative to the support frame 36, such as a back (fowler) section 41, a seat section 43, a leg section 45, and a foot section 47. The patient support deck 38 provides a patient support surface 42 upon which the patient is supported.

A mattress (not shown) is disposed on the patient support deck 38 during use. The mattress comprises a secondary patient support surface upon which the patient is supported. The base 34, support frame 36, patient support deck 38, and patient support surfaces 42 each have a head end and a foot end corresponding to designated placement of the patient's head and feet on the patient transport apparatus 30. The base 34 comprises a longitudinal axis L1 along its length from the head end to the foot end. The base 34 also comprises a vertical axis V arranged crosswise (e.g., perpendicularly) to the longitudinal axis L1 along which the support frame 36 is lifted and lowered relative to the base 34. The construction of the support structure 32 may take on any known or conventional design, and is not limited to that specifically set forth above. In addition, the mattress may be omitted in certain embodiments, such that the patient rests directly on the patient support surface 42.

Patient barriers, such as side rails 44, 46, 48, 50 are coupled to the support frame 36 and/or patient support deck 38 and are thereby supported by the base 34. A first side rail 44 is positioned at a right head end. A second side rail 46 is positioned at a right foot end. A third side rail 48 is positioned at a left head end. A fourth side rail 50 is positioned at a left foot end. In the embodiment shown, the head end side rails 44, 48 are mounted to the back section 41 for movement with the back section 41. The foot end side rails 46, 50 are mounted to the support frame 36 for movement with the support frame 36. If the patient transport apparatus 30 is a stretcher or a cot, there may be fewer side rails. The side rails 44, 46, 48, 50 are movable relative to the back section 41/support frame 36 to a raised position in which they block ingress and egress into and out of the patient transport apparatus 30, one or more intermediate positions, and a lowered position in which they are not an obstacle to such ingress and egress. In the embodiment shown, the side rails 44, 46, 48, 50 are connected to the back section 41 and/or the support frame 36 by pivotal support arms to form four bar linkages. Such side rails and the manner in which they may be raised/lowered are shown and described in U.S. Patent Pub. No. 2017/0172829, filed on Dec. 15, 2016 and entitled "Powered Side Rail For A Patient Support Apparatus," hereby incorporated by reference in its entirety.

A headboard 52 and a footboard 54 are coupled to the support frame 36. The headboard 52 and footboard 54 may be coupled to any location on the patient transport apparatus 30, such as the support frame 36 or the base 34. In still other embodiments, the patient transport apparatus 30 does not include the headboard 52 and/or the footboard 54.

Caregiver interfaces 56, such as handles, are shown integrated into the headboard 52, footboard 54, and side rails 44, 46, 48, 50 to facilitate movement of the patient transport apparatus 30 over a floor surface. Additional caregiver interfaces 56 may be integrated into other components of the patient transport apparatus 30. The caregiver interfaces 56 are graspable by the caregiver to manipulate the patient transport apparatus 30 for movement, to move the side rails 44, 46, 48, 50, and the like.

Other forms of the caregiver interface 56 are also contemplated. The caregiver interface may comprise one or more handles coupled to the support frame 36. The caregiver interface may simply be a surface on the patient transport apparatus 30 upon which the caregiver logically applies force to cause movement of the patient transport apparatus 30 in one or more directions, also referred to as a push location. This may comprise one or more surfaces on the support frame 36 or base 34. This could also comprise one or more surfaces on or adjacent to the headboard 52, footboard 54, and/or side rails 44, 46, 48, 50. In other embodiments, the caregiver interface may comprise separate handles for each hand of the caregiver. For example, the caregiver interface may comprise two handles.

A wheel assembly 57 is coupled to the base 34 to facilitate transport over the floor surface. The wheel assembly 57 includes a plurality of wheels 58. Each wheel 58 includes a braking mechanism 62 (also shown in FIGS. 18-19) to brake the wheel 58. The wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. It should be understood that various configurations of the caster assemblies 60 are contemplated. In addition, in some embodiments, the wheels 58 are not caster wheels and may be non-steerable, steerable, non-powered, powered, or combinations thereof. Additional wheels are also contemplated. For example, the patient transport apparatus 30 may comprise four non-powered, non-steerable wheels, along with one or more powered wheels. In some cases, the patient transport apparatus 30 may not include any wheels.

In other embodiments, one or more auxiliary wheels (powered or non-powered), which are movable between stowed positions and deployed positions, may be coupled to the support structure 32. In some cases, when these auxiliary wheels are located between caster assemblies 60 and contact the floor surface in the deployed position, they cause two of the caster assemblies 60 to be lifted off the floor surface thereby shortening a wheel base of the patient transport apparatus 30. A fifth wheel may also be arranged substantially in a center of the base 34.

Referring to FIGS. 2-5, the patient transport apparatus 30 is shown with the support frame 36 and the patient support deck 38 removed for illustration purposes. In the illustrated embodiment, the patient transport apparatus 30 includes an electro-mechanical braking system 64 to enable a user such as, for example, a caregiver to selectively engage the braking mechanism 62 of the wheels 58. The electro-mechanical braking system 64 includes a linkage assembly 66 that is coupled to the wheel assembly 57, a manual actuator 68 that is coupled to the linkage assembly 66, and an electrical braking assembly 70 that is coupled to the linkage assembly 66. One such patient transport apparatus which may be used with the electro-mechanical braking system 64 described herein is shown and described in U.S. patent application Ser. No. 14/256,568, filed on Apr. 18, 2014 and entitled "Patient Support Apparatus With Braking System", now U.S. Pat. No. 9,555,778, hereby incorporated by reference in its entirety.

In the illustrated embodiment, the linkage assembly 66 is coupled to one or more braking mechanisms 62 and is arranged to place the braking mechanism 62 in a braked state 61 (shown in FIG. 18) in which the braking mechanism 62 brakes a corresponding wheel 58 and a released state 63 (shown in FIG. 19) in which the braking mechanism 62 is released from braking the wheel 58. The linkage assembly 66 may also be coupled to one or more steer lock mechanisms (not shown) to place the one or more steer lock mechanisms in a steer locked state in which one or more of the wheels 58 are prevented from swiveling. The released state may also be referred to as a neutral state. The manual actuator 68 is coupled to the linkage assembly 66 to move the linkage assembly 66 manually to place the braking mechanism 62 in the braked state and in the released state, or to place the steer lock mechanism in the steer locked state. For example, referring to FIG. 5, in one embodiment, the manual actuator 68 may be operated by a caregiver to move the linkage assembly 66 in a first direction 72 which causes the braking mechanism 62 to move to the braked state to brake the wheel 58 and to move the linkage assembly 66 in an opposite second direction 74 which causes the braking mechanism 62 to move to the released state to release the wheel 58. Further movement in the second direction 74 could be used to place one or more of the wheels 58 in the steer locked state.

The electrical braking assembly 70 is also coupled to the linkage assembly 66 and configured to move the linkage assembly 66 to place the braking mechanism 62 in the braked state and in the released state. The electrical braking assembly 70 is configured to operate to a first position, a second position, and a home position (and in some cases a third position if steer lock is employed). The electrical braking assembly 70 operates to the first position to cause the linkage assembly 66 to move in the first direction 72 to place the braking mechanism 62 in the braked state, and operates to the second position to cause the linkage assembly 66 to move in the second direction 74 to place the braking mechanism 62 in the released state. The electrical braking assembly 70 operates in the home position to allow the linkage assembly to move freely and enable the braking mechanism 62 to be manually actuated with the manual actuator 68.

Figure 5:
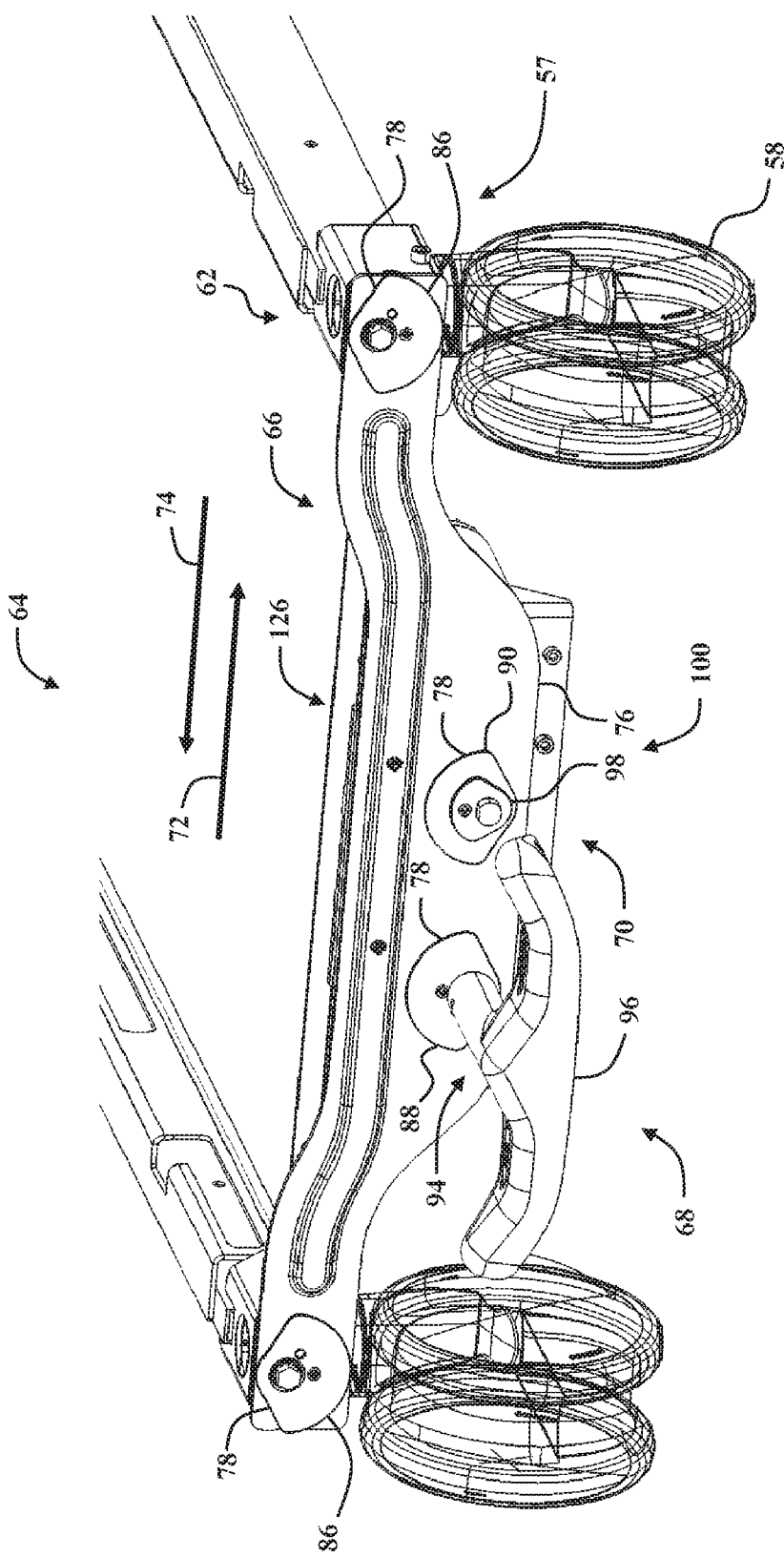
FIG. 5 is an enlarged perspective view of the patient transport apparatus taken along Area 5 shown in FIG. 2 and illustrating the electro-mechanical braking system.
Figure 6:
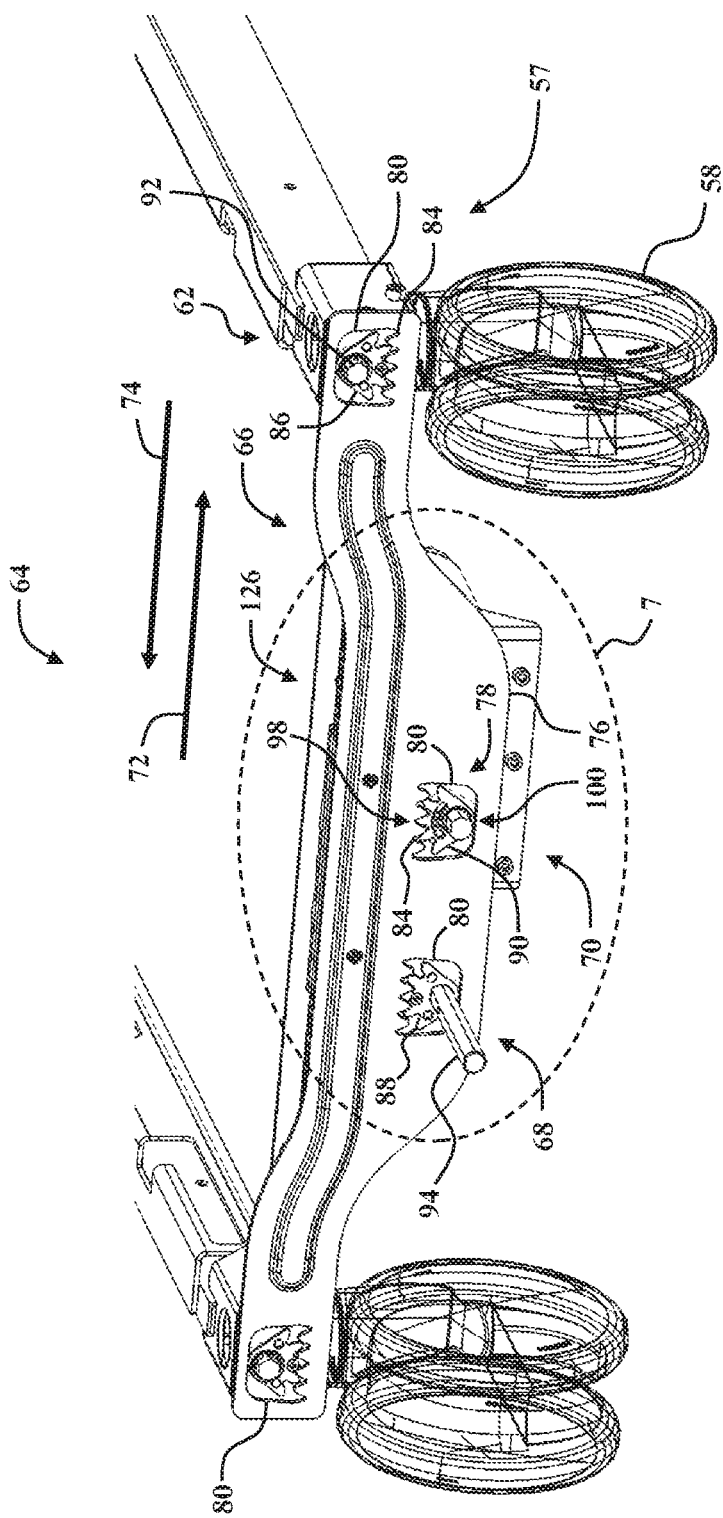
FIG. 6 is a perspective view of a portion of the electro-mechanical braking system shown in FIG. 5.
Figure 7:
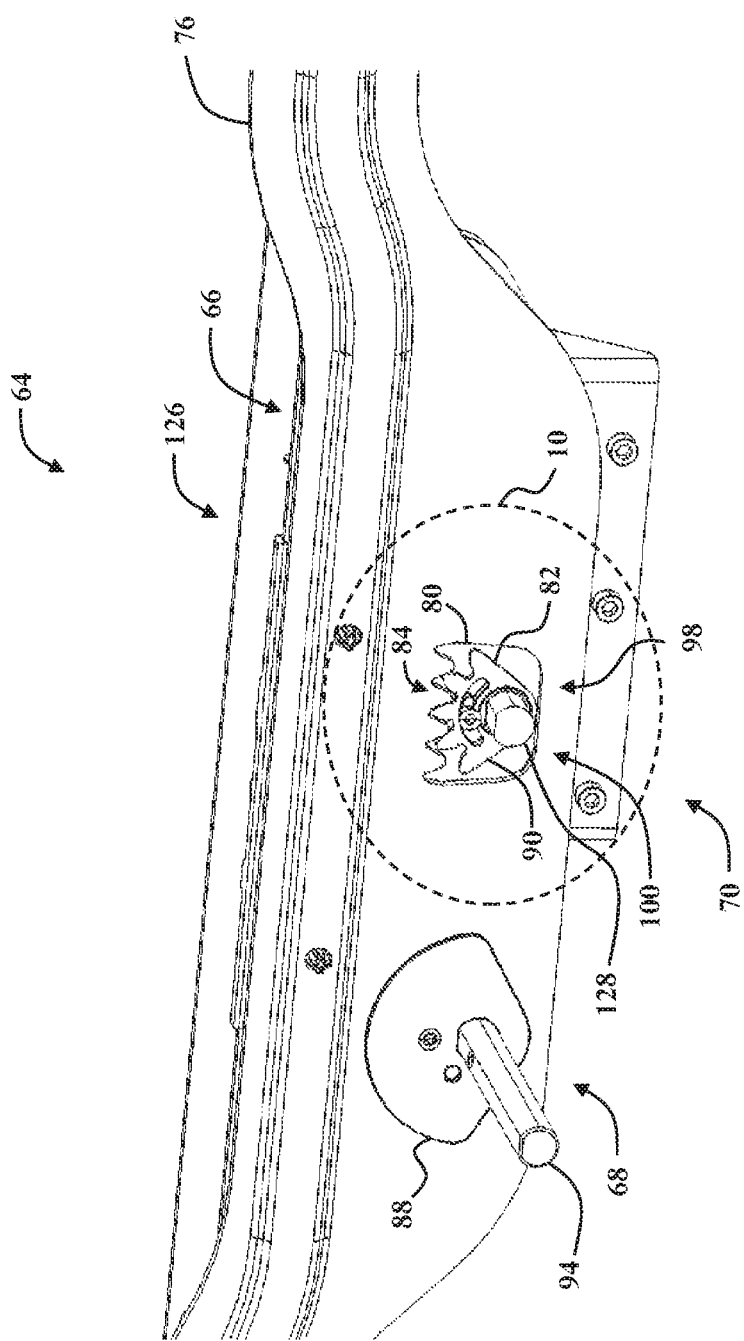
FIG. 7 is an enlarged perspective view of the electro-mechanical braking system taken along Area 7 shown in FIG. 6 illustrating a driving assembly.
Figure 8:
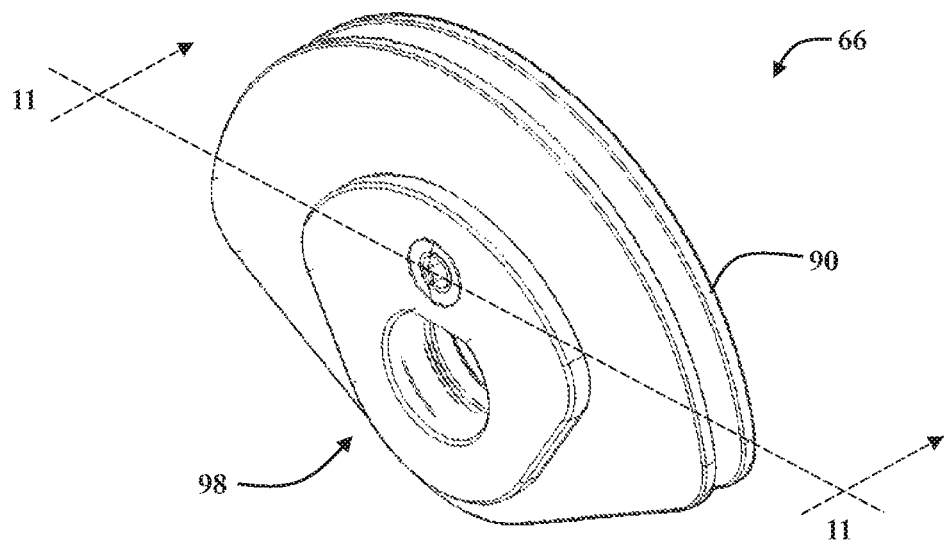
FIG. 8 is a perspective view of an actuation member than may be used with the driving assembly.
Figure 9:
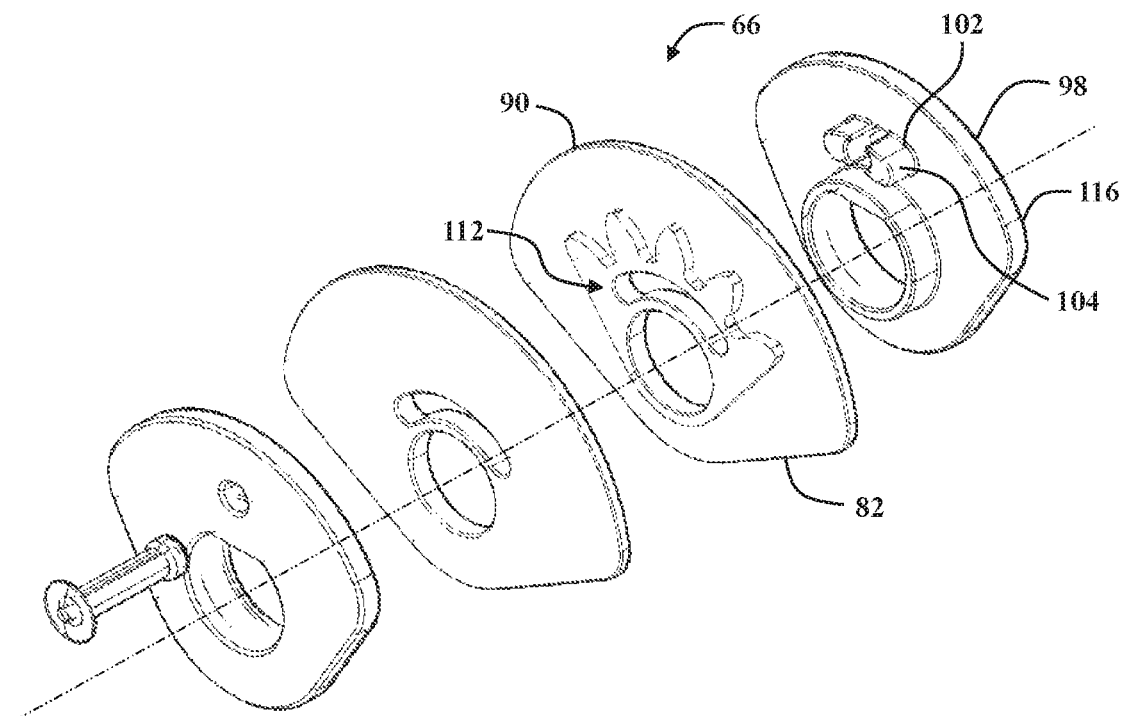
FIG. 9 is an exploded view of the actuation member shown in FIG. 8.
Figure 10:
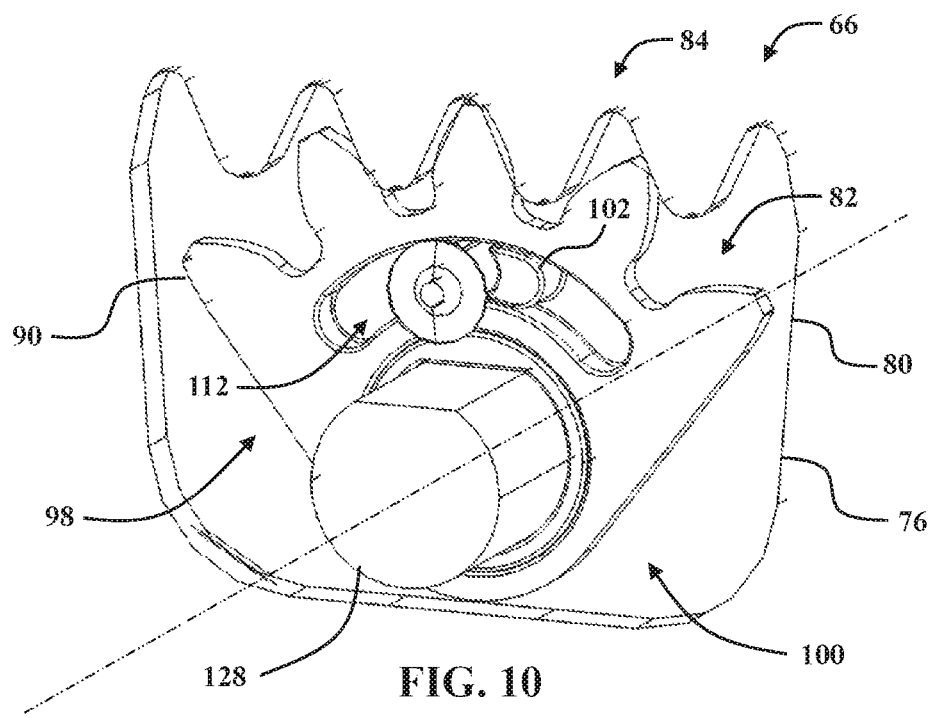
FIG. 10 is an enlarged perspective view of the braking system taken along Area 10 shown in FIG. 7.
Figure 11:
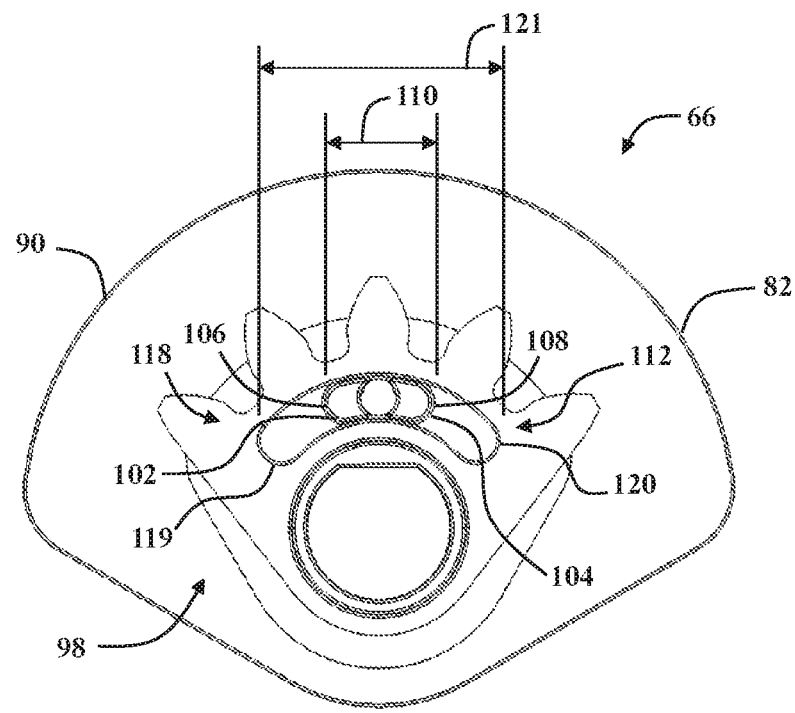
FIG. 11 is a sectional view of the actuation member taken along sectional line 11-11 shown in FIG. 8.

Referring to FIGS. 5-7, in the illustrated embodiment, the linkage assembly 66 includes a link 76 and a plurality of actuation members 78 that contact the link 76 such that a movement of the actuation members 78 causes a movement of the link 76 and movement of the link 76 causes a movement of the actuation members 78. The link 76 includes a plurality of engagement slots 80 extending through an outer surface of the link 76. Each engagement slot 80 is sized and shaped to receive a corresponding actuation member 78 therein. In one embodiment, one or more actuation members 78 may include a sector gear 82. The engagement slot 80 may include a plurality engagement teeth 84 that are configured to contact the sector gear 82 with the sector gear 82 positioned within the engagement slot 80 such that a movement of the sector gear 82 causes movement of the link 76.

In the illustrated embodiment, the linkage assembly 66 includes one or more braking mechanism actuation members 86, one or more manual actuation members 88, and one or more driving actuation members 90. Each braking mechanism actuation member 86 is coupled to the braking mechanism 62 of the wheel assembly 57. As shown in FIG. 6, the wheel assembly 57 includes a hex shaft 92 that is coupled to a corresponding braking mechanism 62 to move the braking mechanism 62 between the braked state and the released state. The braking mechanism actuation member 86 is coupled to the hex shaft 92 such that a rotation of the braking mechanism actuation member 86 causes a rotation of the hex shaft 92. For example, in one embodiment, the braking mechanism actuation member 86 includes a sector gear 82 that is positioned within an engagement slot 80 to engage the corresponding engagement teeth 84. During operation of the braking system 64, as the link 76 is moved in the first direction 72, the link 76 causes a movement of the braking mechanism actuation member 86 which rotates the hex shaft 92 in a counter-clockwise direction to move the braking mechanism 62 to the braked state 61 (shown in FIG. 18). As the link 76 is moved in the second direction 74, the link 76 moves the braking mechanism actuation member 86 to rotate the hex shaft 92 in a clockwise direction to move the braking mechanism 62 to the released state 63 (shown in FIG. 19). Further movement of the hex shaft 92 in the clockwise direction, in some embodiments, moves the steer lock mechanism to the steer locked state.

Referring to FIGS. 5-10, the manual actuation member 88 is coupled to the manual actuator 68 to enable the link 76 to be moved in the first direction 72 and the second direction 74 manually. In the illustrated embodiment, the manual actuator 68 includes a manual actuation shaft 94 and a brake pedal 96 that is coupled to the manual actuation shaft 94. The manual actuation shaft 94 is coupled to the manual actuation member 88 such that a rotation of the manual actuation shaft 94 causes a rotation of the manual actuation member 88 which causes the link 76 to move in the first direction 72 and the second direction 74. For example, in one embodiment, the manual actuation member 88 includes a sector gear 82 positioned within an engagement slot 80. The sector gear 82 is configured to contact the engagement teeth 84 of the engagement slot 80 such that a rotation of the manual actuation member 88 causes a movement of the link 76. During operation, a caregiver may operate the brake pedal 96 to rotate the manual actuation shaft 94 and the manual actuation member 88 in a clockwise direction to move the link 76 in the first direction 72 to cause the braking mechanism 62 to move to the braked state. The caregiver may also operate the brake pedal 96 to rotate the manual actuation shaft 94 and the manual actuation member 88 in a counter-clockwise direction to move the link 76 in the second direction 74 to cause the braking mechanism 62 to move to the released state. Further movement in the second direction 74, in some embodiments, causes the steer lock mechanism to move to the steer locked state.

The linkage assembly 66 includes a driving actuation member 90 that is coupled to electrical braking assembly 70 to enable the electrical braking assembly 70 to move the link 76 in the first and second directions 72, 74. The electrical braking assembly 70 includes a driving assembly 98 that is coupled to the linkage assembly 66 and an actuator assembly 100 that is coupled to the driving assembly 98. The driving assembly 98 is coupled to the driving actuation member 90 to cause a movement of the driving actuation member 90. In one embodiment, the driving actuation member 90 may include a sector gear 82 that is positioned within an engagement slot 80 and is configured to contact the engagement teeth of the engagement slot 80 such that a rotation of the driving actuation member 90 causes a movement of the link 76.

Referring to FIGS. 8-11, the driving assembly 98 comprises a positioning member 102. In one embodiment, the positioning member 102 includes a body 104 that extends between a first end 106 and a second end 108 and has a length 110 defined between the first end 106 and the second end 108. The linkage assembly 66 includes a positioning slot 112 that is configured to receive the positioning member 102 therein. The positioning slot 112 provides a travel path 114 (see FIGS. 12-14) for the positioning member 102 and is sized so that the positioning member 102 is movable along the travel path 114. In one embodiment, the driving assembly 98 includes a driving member 116 that is coupled to the driving actuation member 90 such that the driving actuation member 90 may move with respect to the driving member 116. In one embodiment, the driving actuation member 90 is rotatably coupled to the driving member 116. The driving member 116 includes the positioning member 102 that extends outwardly from an outer surface of the driving member 116. The driving actuation member 90 includes the positioning slot 112 that extends through an outer surface of the driving actuation member 90 and is sized and shaped to receive the positioning member 102 therein. The positioning member 102 is configured to contact an inner surface (e.g., ends of the travel path) of the positioning slot 112 to cause a movement of the driving actuation member 90.

As shown in FIGS. 10-14, the positioning slot 112 defines a cavity 118 that extends between a first end 119 and a second end 120 and includes a length 121 defined between the first end 119 and the second end 120. The positioning slot 112 provides the travel path 114 that is sized so that the positioning member 102 is movable along the travel path 114. The positioning member 102 is movable to a first position 122, a second position 123, a third position 124, and a home position 125 between the first and second positions 122, 123. The travel path 114 is sized so that the positioning member 102 is movable along the travel path 114 when returning to the home position 125, such as back to a center position when the braking mechanism 62 is in the released state (neutral). The length 121 of the positioning slot 112 is longer than the length 110 of the positioning member 102 such that the driving actuation member 90 is freely rotatable with respect to the driving member 116 with the positioning member 102 in the home position 125.

Figure 12:
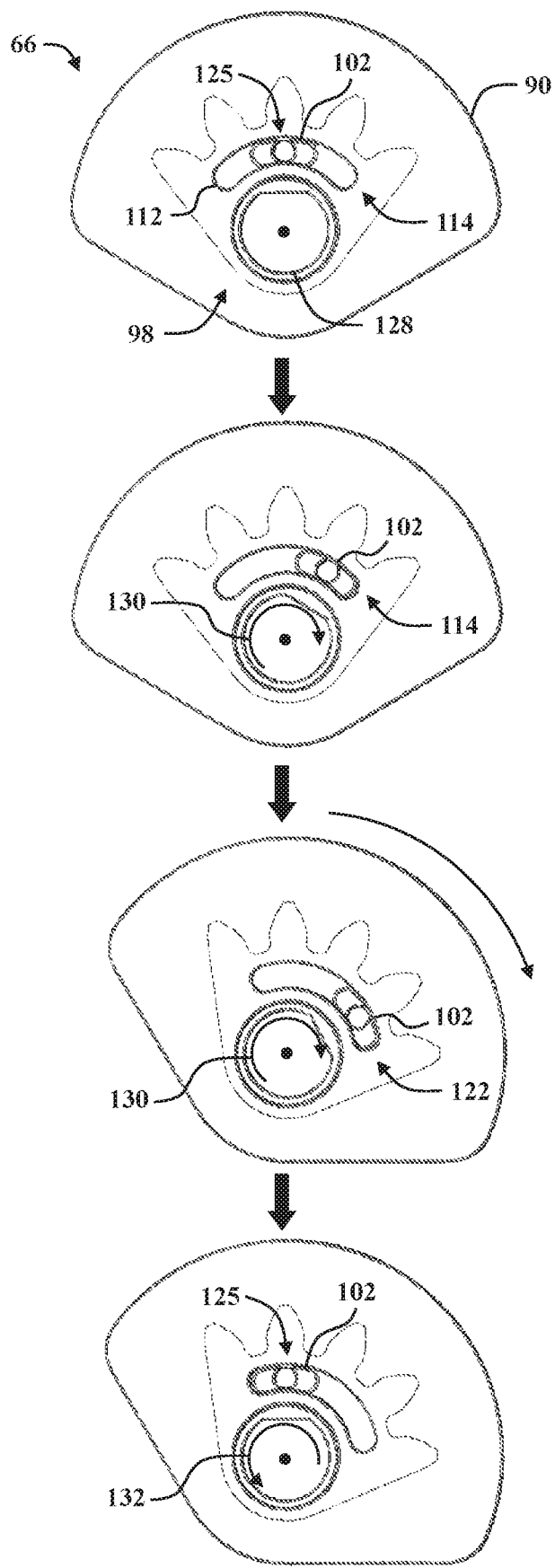
FIG. 12 is a sequence of views of the actuation member shown in FIG. 11 illustrating a movement of the actuation member from a home position to a first position and a return to the home position.

FIG. 12 shows a sequence of the positioning member 102 moving from the home position 125, to the first position 122, and back to the home position 125. In the embodiment shown, with the positioning member 102 in the home position 125 and the braking mechanism 62 in the released state, the driving actuation member 90 may move freely with respect to the driving member 116 and the link 76 is allowed to move freely in both the first and second directions 72, 74 to enable seamless manual actuation of the brake mechanism 162 or the steer lock mechanism. For example, with the positioning member 102 in the home position 125, the caregiver may operate the manual actuator 68 to move the link 76 along the first and second directions 72, 74 to operate the braking mechanism 62 without moving the driving member 116 or operating the electrical braking assembly 70. As the positioning member 102 moves along the travel path 114 from the home position 125 towards the first position 122, the positioning member 102 contacts the inner surface of the positioning slot 112 at an end of the travel path 114 which causes the driving actuation member 90 to move the link 76 in the first direction 72 to place the brake mechanism 62 in the braked state. Thereafter, the positioning member 102 is returned to the home position 125 as shown at the end of the sequence in FIG. 12 to enable manual release of the braking mechanism 62 without interference by the positioning member 102.

Figure 13:
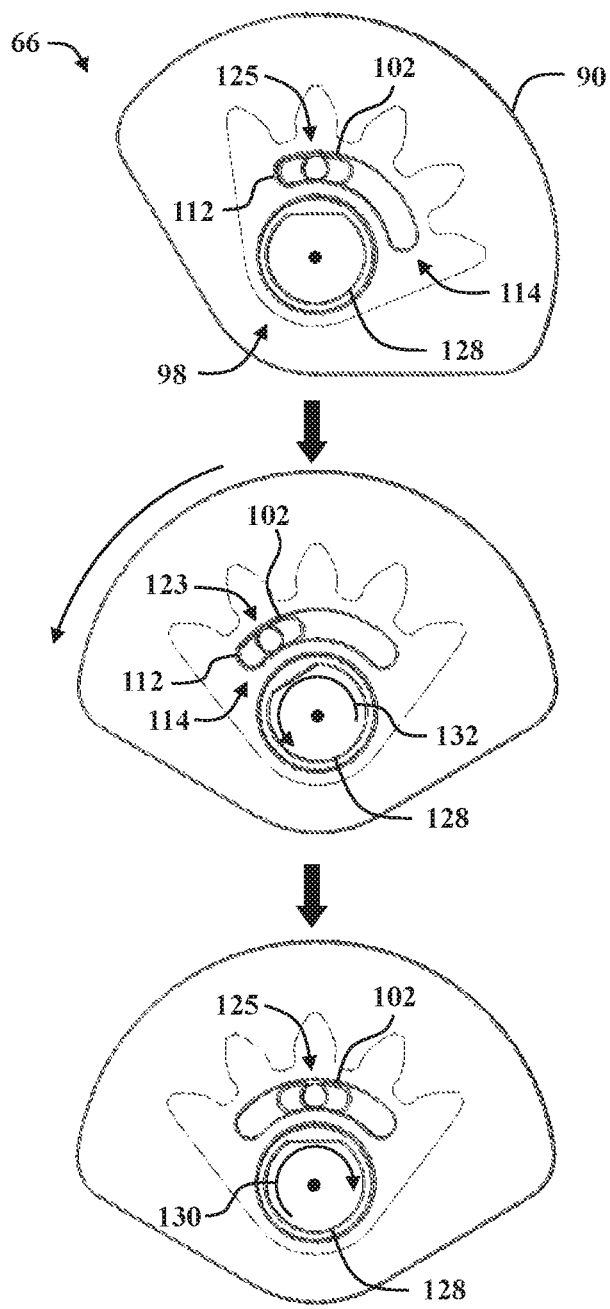
FIG. 13 is a sequence of views of the actuation member shown in FIG. 11 illustrating a movement of the actuation member from the home position to a second position and a return to the home position.
Figure 14:
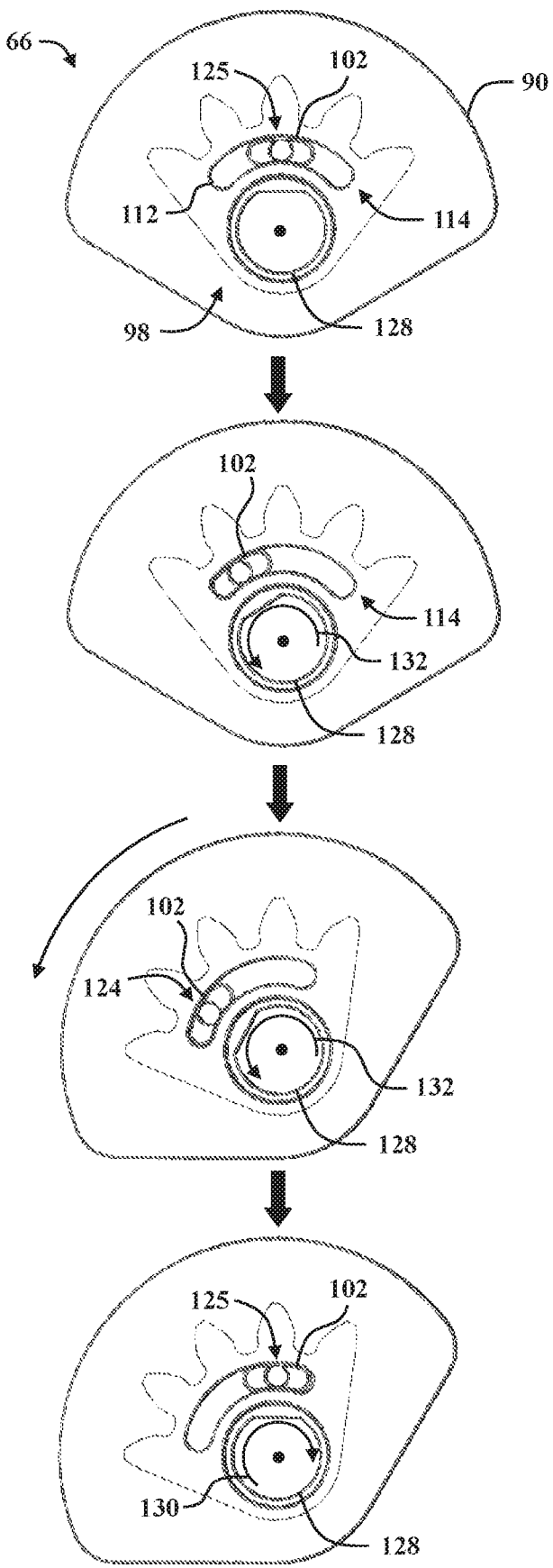
FIG. 14 is a sequence of views of the actuation member shown in FIG. 11 illustrating a movement of the actuation member from the home position to a third position and a return to the home position.

Referring to FIG. 13, which follows the sequence of FIG. 12, as the positioning member 102 moves from the home position 125 to the second position 123, the positioning member 102 contacts the inner surface of the positioning slot 112 at the opposite end of the travel path 114 which causes the driving actuation member 90 to move the link 76 in the second direction 74 to place the brake mechanism 62 in the released state. Thereafter the positioning member 102 returns back to the home position 125 as shown at the end of the sequence in FIG. 13. FIG. 14 shows a similar sequence as FIG. 12, except moving the positioning member 102 from the home position 125 to the third position 124 to move the steer lock mechanism to the steer locked state. Thereafter, as before, the positioning member 102 returns to the home position 125 at the end of the sequence. Releasing of the steer lock mechanism back to the released state (neutral) is a mirror image of the sequence shown in FIG. 13.

Each of the sequences shown in FIGS. 12, 13, 14 may be responsive to user input via a sensing device or other user input device as described further below (e.g., input to brake the wheels, release the wheels, or steer lock the wheels) and may occur within a predetermined time period, such as within 15 seconds, within 10 seconds, within 5 seconds, within 3 seconds, or within shorter or longer time periods.

In the illustrated embodiment, the actuator assembly 100 is configured to move the driving assembly to the first position 122, the second position 123, the third position 124, and the home position 125 between the first and second positions 122, 123. The movement of the driving assembly 98 to the first position 122 causes the linkage assembly 66 to place the braking mechanism 62 in the braked state 61 (shown in FIG. 18). The movement of the driving assembly 98 to the second position 123 causes the linkage assembly 66 to place the braking mechanism 62 in the released state 63 (shown in FIG. 19). In addition, the movement of the driving assembly 98 to the home position 125 allows the linkage assembly 66 to move relative to the driving assembly 98 to enable the braking mechanism 62 to be manually actuated with the manual actuator 68.

The actuator assembly 100 may include linear actuators, rotary actuators, or other types of actuators. The actuator assembly 100 be electrically operated, electro-hydraulic, hydraulic, pneumatic, and the like. Referring to FIGS. 3, 7, 10, and 15, in the illustrated embodiment, the actuator assembly 100 includes a motor 126 (e.g., an electric motor) and a drive shaft 128 (see FIG. 7) that is rotatably coupled to the motor 126. The driving assembly 98 is coupled to the drive shaft 128 such that a rotation of the drive shaft 128 rotates the positioning member 102. For example, as shown in FIGS. 12-14, the motor 126 may rotate the drive shaft 128 in a first rotational direction 130 to move the positioning member 102 along the travel path 114 and from the home position 125 to the first position 122. Similarly, the motor 126 may rotate the drive shaft 128 in the first rotational direction 130 to move the positioning member 102 along the travel path 114 from the second position 123 to the home position 125 and/or to the first position 122. The motor 126 may rotate the drive shaft 128 in an opposite second rotational direction 132 to move the positioning member 102 along the travel path 114 and from the home position 125 to the second position 123 and/or to the third position 124. In addition, the motor 126 may rotate the drive shaft 128 in the second rotational direction 132 to move the positioning member 102 along the travel path 114 from the first position 122 to the home position 125 and/or to the second position 123, and/or the third position 124. The link 76 is coupled to driving actuation member 90 and to the braking mechanism 62 such that a rotation of the driving actuation member 90 causes the link 76 to operate the braking mechanism 62 to place the braking mechanism 62 in the braked state and the released state or to place the steer lock mechanism in the steer locked state.

Figure 15:
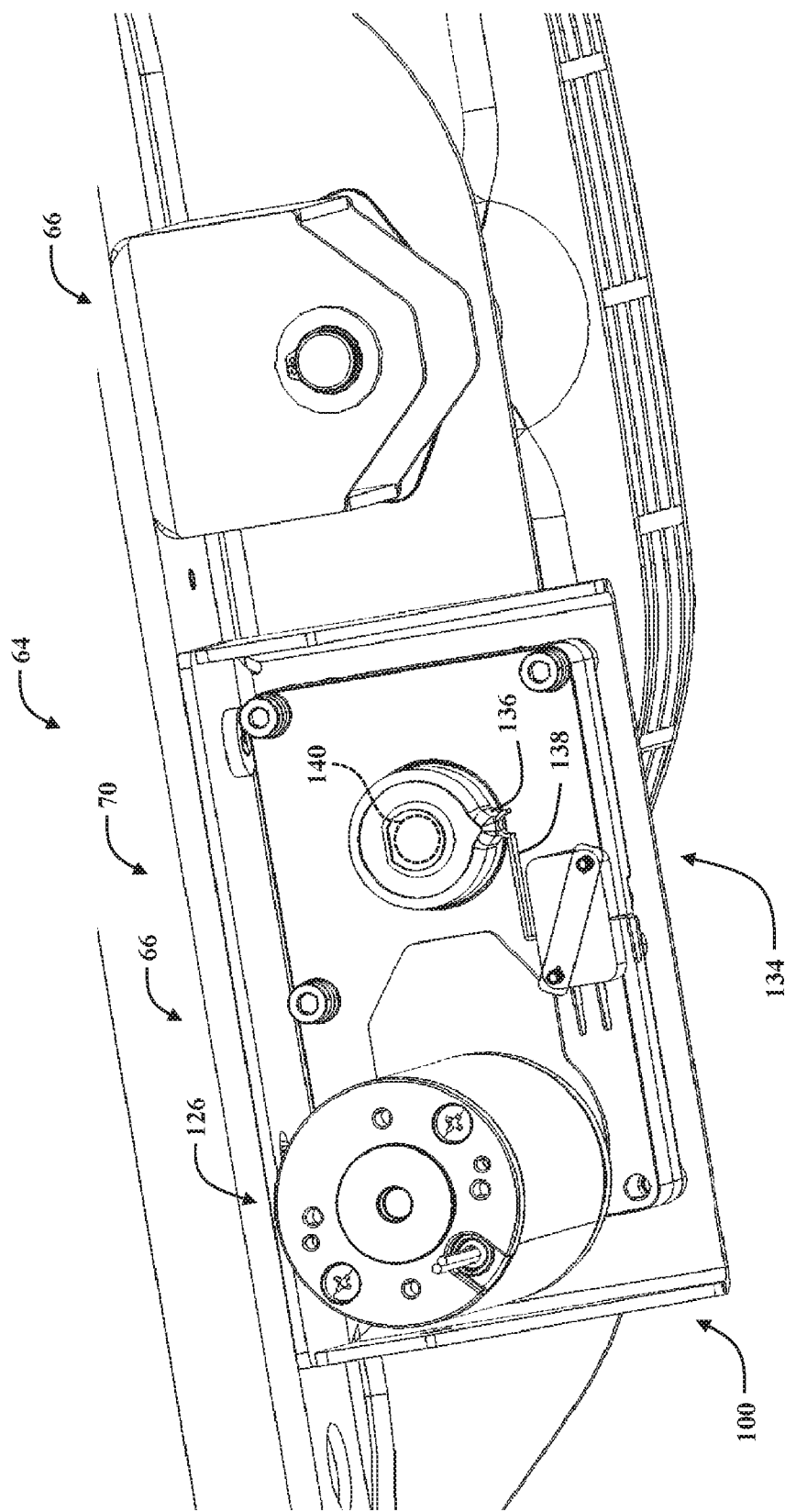
FIG. 15 is a perspective view of a portion of the electrical braking system.

Referring to FIG. 15, in the illustrated embodiment, the electrical braking assembly 70 includes a sensor assembly 134 that is configured to sense a position of the positioning member 102. The sensor assembly 134 includes a position indicator 136 and a sensor arm 138. The position indicator 136 is orientated with respect to the positioning member 102. In one embodiment, the position indicator 136 is coupled to the drive shaft 128 such that a rotation of the drive shaft 128 rotates the position indicator 136. The sensor arm 138 is configured to contact the position indicator 136 with the positioning member 102 in the home position 125. A controller 144 is coupled to a sensor (e.g., limit switch or other suitable sensor) attached to the sensor arm 138 to determine when the drive shaft 128 and the positioning member 102 have reached the home position. The controller 144 is coupled to the motor 126 to control operation of the motor 126 based on input from the sensor so that the motor 126 is able to rotate the drive shaft 128 and move the positioning member 102 as needed to place the braking mechanism 62 in the braked state, released state, or to place the steer lock mechanism in the steer locked state.

The electrical braking assembly 70 may also include a torque limiting device 140 that is operable between the motor 126 and the positioning member 102 to limit an amount of torque being applied to the positioning member 102 and/or the driving member 116 by the motor 126. The torque limiting device 140 may include a slip clutch, a spring loaded coupling, a belt drive, and/or any suitable torque limiting device that operates to limit the amount of torque being applied by the motor 126 to the drive shaft 128.

When the motor 126 is driving the linkage assembly 66 via the driving assembly 98 to a desired state, a caregiver may step on the manual brake pedal 96 with great load. During this scenario, without the torque limiting device 140, and owing to the motor 126 being largely non-backdriveable, damage could be caused to mechanical components of the brake system 64, such as the sector gears 82, teeth 84, or the like. When the motor 126 is acting to change a state of the brake system 64, the torque limiting device 140 (also referred to as a temporary mechanical fuse) allows the linkage assembly 66 to "slip" relative to the motor 126 during the large load scenario, i.e., the linkage assembly 66 moves the positioning member 102 manually by virtue of the positioning member 102 being decoupled from the motor 126 via the torque limiting device 140. In effect, manual actuation overrides electrical actuation. After the large load subsides and the torque limiting device 140 returns to normal operation transmitting torque from the motor 126 to the positioning member 102, the control system and controller 144 described further below senses the system state and continues to drive the brake system 64 to the desired states as before.

Figure 4:
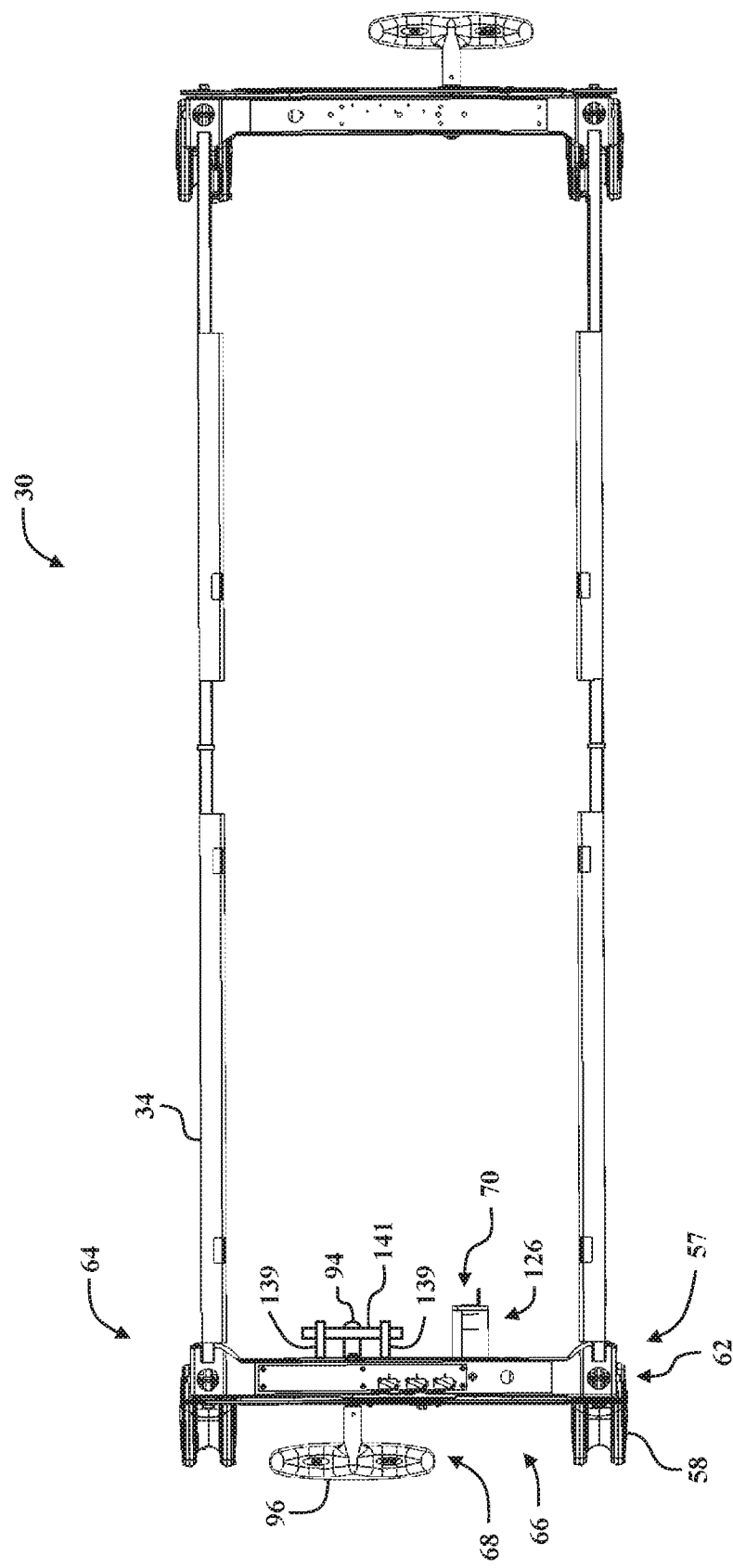
FIG. 4 is a top view of a portion of the patient transport apparatus illustrating the electro-mechanical braking system.
Figure 4A:
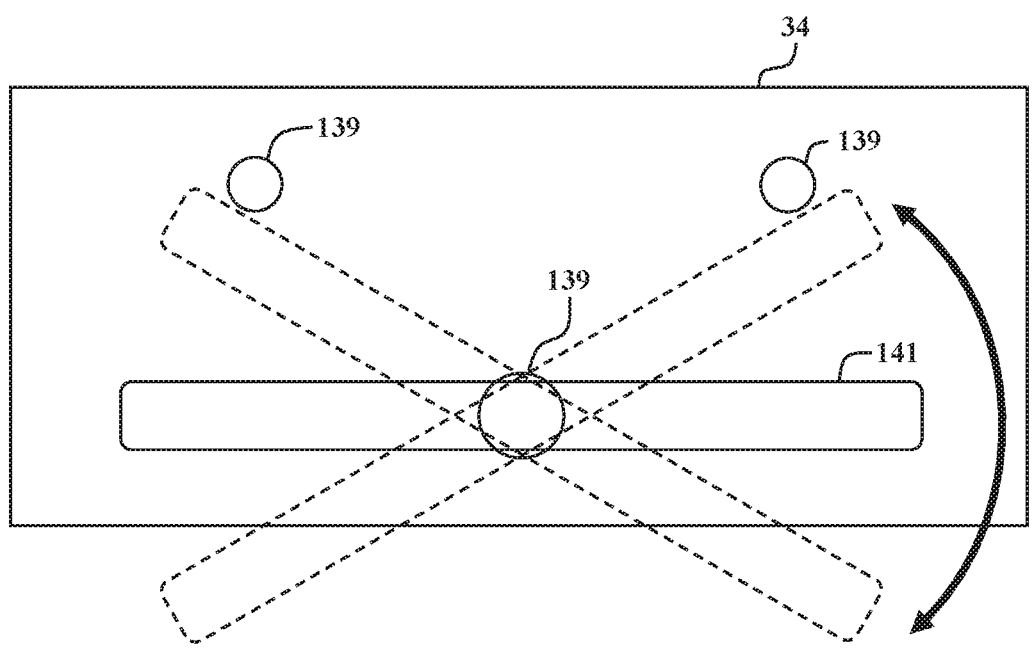
FIG. 4A illustrates hard stops for the electro-mechanical braking system.

In addition, or as an alternative to the torque limiting device 140, hard stops 139 (see FIGS. 4 and 4A) could be employed for the manual foot pedal 96 so that excessive loads on the manual foot pedal 96 are grounded to the base 34 or other part of the support structure 32 before causing damage to the mechanical components of the brake system 64. Such hard stops 139 could merely be a portion of the base 34 or other part of the support structure 32, such as the projections shown in FIG. 4. A rigid stop member 141 could be fixed to the manual actuation shaft 94 and arranged to engage the hard stops 139 during excessive pedal movement so that movement of the manual brake pedal 96 is limited. The rigid stop member 141 may comprise arms that extend on opposite sides from the manual actuation shaft 94 (in a manner much like the pedal 96) but beneath the hard stops 139 so that excessive rotation of the manual foot pedal 96 in one direction causes the stop member 141 to engage one of the hard stops 139 and excessive rotation of the manual foot pedal 96 in the opposite direction causes the stop member 141 to engage the other of the hard stops 139. The hard stops 139 are arranged so that normal actuation of the manual foot pedal 96 to move between the braked, released, and steer locked states is not impeded, but merely prevents over rotation of the manual foot pedal 96 and provides a load path for excessive loads.

Figure 16:
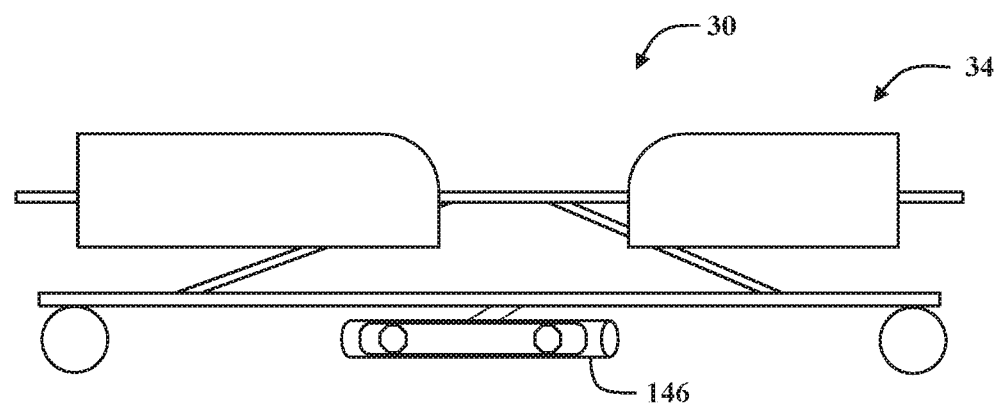
FIG. 16 is a view of a portion of the patient transport apparatus illustrating a sensing device that may be used with the electro-mechanical braking system.
Figure 17:
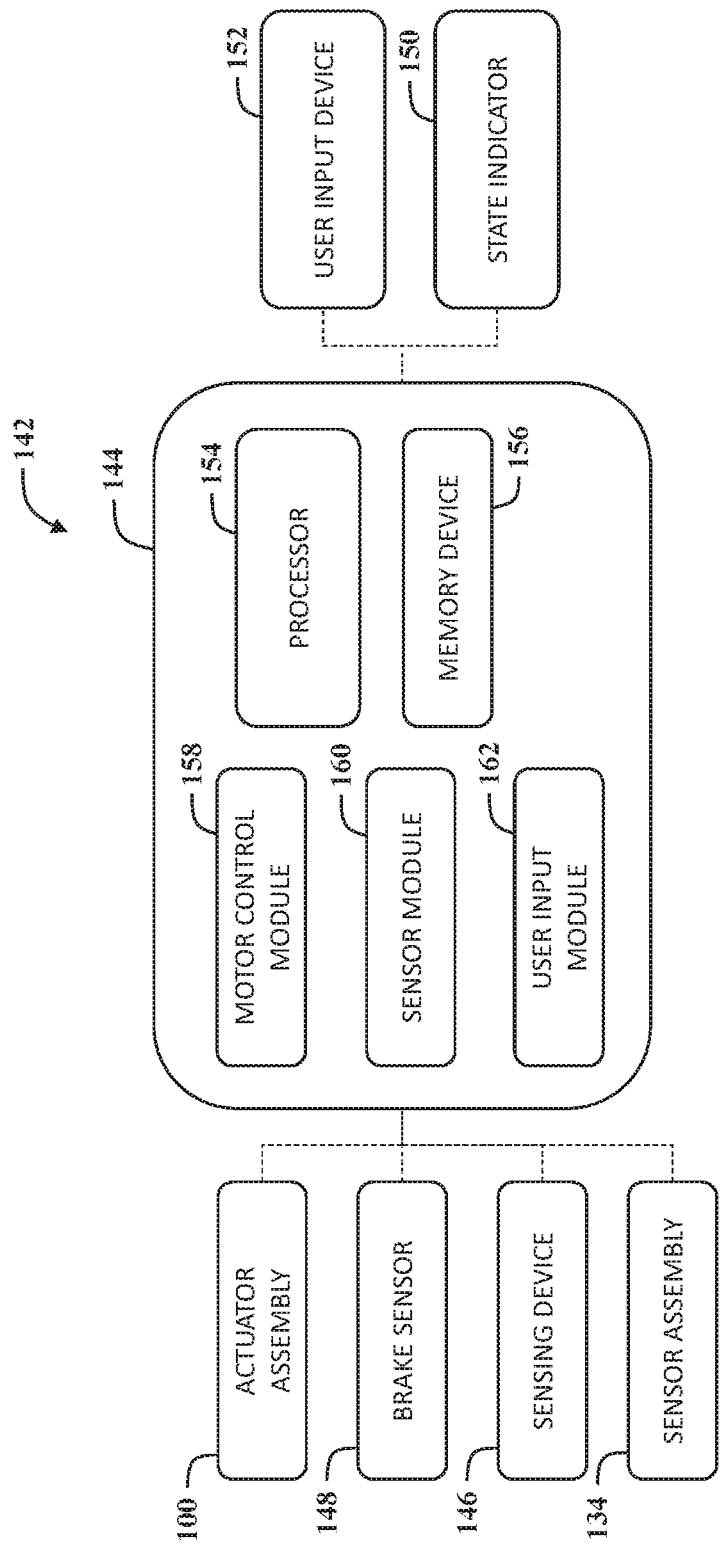
FIG. 17 is a block diagram illustrating a control assembly that may be used with the electro-mechanical braking system.

Referring to FIGS. 16, and 17, in the illustrated embodiment, the patient transport apparatus 30 includes a control assembly 142 to control operations of the braking system 64. The control assembly 142 comprises the controller 144 having one or more microprocessors, microcontrollers, field programmable gate arrays, systems on a chip, discrete circuitry, and/or other suitable hardware, software, or firmware that is capable of carrying out the functions described herein. The controller 144 may be carried on-board the patient transport apparatus 30, or may be remotely located. In one embodiment, the controller 144 is mounted to the base 34. In other embodiments, the controller 144 is mounted to the footboard 54. Power to the electrical braking assembly 70 and/or the controller 144 may be provided by a battery power supply and/or an external power source. The controller 144 is coupled to the electrical braking assembly 70 in a manner that allows the controller 144 to control the actuator assembly 100 (connections shown schematically in FIG. 17). The controller 144 may communicate with the actuator assembly 100 via wired or wireless connections to perform one of more desired functions.

In the illustrated embodiment, the control assembly 142 includes a sensing device 146 that is configured to sense a proximity of a caregiver and operate as a user input device to control operation of the brake system 64. The sensing device 146 may be mounted to the support structure 32 and include a proximity sensor for sensing a proximity of the caregiver. The controller 144 is coupled to the sensing device 146 and the electrical braking assembly 70, and is configured to operate the electrical braking assembly 70 upon receiving a signal from the sensing device 146 indicating a sensed proximity of the caregiver. The sensing device 146 may also include gesture sensing devices for monitoring motion of hands, feet, or other body parts of the caregiver (such as through a camera), a microphone for receiving voice activation commands, a foot pedal, and a sensor (e.g., infrared sensor such as a light bar or light beam to sense a caregiver's body part, ultrasonic sensor, etc.).

The sensing device 146 may also include a projected laser icon which when a foot is placed in a predetermined region causes activation of the electrical braking assembly 70. A "brake" logo may be projected onto the floor under or adjacent to the base 34. When the caregiver places their foot in the region and/or taps on the projected logo, the control system registers the input to activate or deactivate the braking mechanism 62.

The sensing device 146 may also include a brake bar placed in specified locations under the base 34 attached to the base frame 35, and may not require physical depression to activate. The caregiver would touch the bar with any part of their foot or leg with such contact registering as an input. The bar could vibrate to acknowledge the input (e.g., via piezoelectric elements on the base frame 35 that are coupled to the controller 144). The bar could also emit color to represent the current state and/or available states (i.e., the color or other indicia could indicate the braked state if the current state is the released state). The sensing device 146 may also be integrated into the manual foot pedal 96 so that the manual foot pedal 96 can be depressed for manual actuation, merely touched on one side or the other for electrical actuation, and/or responsive to user proximity for electrical actuation.

The sensing device 146 may also include a proximity brake that is controlled through the use of a proximity sensor. When a foot or leg of the caregiver enters any region under the base 34, the patient transport apparatus 30 would register that as an input. Instead of finding a specific zone or button, the simple motion of the leg under the base 34 would activate or deactivate the braking mechanism 62. Such brake systems do not require the caregiver to break their focus or care being given to their patient to find a brake button, and are hands free which enables the caregiver to focus on the patient.

The sensing device 146 may include various sensors including ultrasonic sensors, radar, laser beam disruption, proximity sensors, proximity measurement sensors, proximity zone monitoring sensors, infrared sensors, pressure sensors, haptic sensors, Hall-effect sensors, microswitches, and/or force sensors.

The control assembly 142 also includes a brake sensor 148 coupled to the controller 144. The brake sensor 148 is configured to sense a position of the braking mechanism 62. The brake sensor 148 may be mounted to the braking mechanism 62 for sensing a position of the braking mechanism 62. The brake sensor 148 may also be coupled to the actuator assembly 100 and configured to measure rotations of the motor 126. The brake sensor 148 could also be mounted to the manual actuation shaft 94 and/or the brake pedal 96 to determine a position of the brake pedal 96 and correlate these positions to the braked state, released state, or steer locked state.

The control assembly 142 also includes a state indicator 150 that is coupled to the controller 144. The controller 144 is configured to operate the state indicator 150 to indicate the sensed position of the braking mechanism 62. The state indicator 150 may include a visual indicator, audible indicator, and/or tactile indicator to indicate the sensed state of the braking mechanism 62. The state indicator 150 may be coupled to the manual brake pedal 96, the base 34, the side rails 44, 46, 48, 50, the headboard or 52 or footboard 54, or any part of the patient transport apparatus 30.

The control assembly 142 may include other user input devices 152 that are operated by the caregiver, and which transmit a corresponding input signal to the controller 144. The controller 144 controls operation of the actuator assembly 100 based on the input signal. The user input devices 152 may comprise any device capable of being actuated by the caregiver. The user input devices 152 may be configured to be actuated in a variety of different ways, including but not limited to, mechanical actuation (hand, foot, finger, etc.), hands-free actuation (voice, foot, etc.), and the like. The user input devices 152 may comprise buttons, and may comprise further buttons corresponding to lift, lower, Trendelenburg, reverse Trendelenburg, raise back section 41, lower back section 41, raise leg section 45, lower leg section 45, raise foot section 47, lower foot section 47, etc.

The user input devices 152 may also comprise a gesture sensing device for monitoring motion of hands, feet, or other body parts of the caregiver (such as through a camera), a microphone for receiving voice activation commands, a foot pedal, and a sensor (e.g., infrared sensor such as a light bar or light beam to sense a caregiver's body part, ultrasonic sensor, etc.). Additionally, the buttons/pedals can be physical buttons/pedals or virtually implemented buttons/pedals such as through optical projection or on a touchscreen. The buttons/pedals may also be mechanically connected or drive-by-wire type buttons/pedals where a caregiver applied force actuates a sensor, such as a switch or potentiometer. It should be appreciated that any combination of user input devices 152 may also be utilized. The user input devices 152 may be located on one of the side rails 44, 46, 48, 50, the headboard 52, the footboard 54, or other suitable locations. The user input devices 152 may also be located on a portable electronic device (e.g., iWatch®, iPhone®, iPad®, or similar electronic devices).

In the illustrated embodiment, the controller 144 includes a processor 154 and a memory device 156. Processor 154 includes any suitable programmable circuit which may include one or more systems and microcontrollers, microprocessors, reduced instruction set circuits (RISC), application specific integrated circuits (ASIC), programmable logic circuits (PLC), field programmable gate arrays (FPGA), and any other circuit capable of executing the functions described herein. The above examples are exemplary only, and thus are not intended to limit in any way the definition and/or meaning of the term "processor." Memory device 156 includes a computer readable medium, such as, without limitation, random access memory (RAM), flash memory, a hard disk drive, a solid state drive, a diskette, a flash drive, a compact disc, a digital video disc, and/or any suitable device that enables processor 154 to store, retrieve, and/or execute instructions and/or data.

In the exemplary embodiment, controller 144 includes a motor control module 158 that is coupled to the actuator assembly 100 to control an operation of actuator assembly 100. The motor control module 158 is configured to execute programming code in response to inputs received by the caregiver via the user interface to operate the actuator assembly 100 based on the user input. In addition, controller 144 also includes a sensor module 160 that is coupled to at least one sensor such as, for example, the sensing device 146 and the brake sensor 148. The sensor module 160 is configured to received data from the sensors and transmit the received sensor data to the motor control module 158 to facilitate operating the electrical braking assembly 70. Each sensor may transmit a signal continuously, periodically, or only once and/or any other signal timing that enables the controller 144 to function as described herein. Moreover, each sensor may transmit a signal either in an analog form or in a digital form.

The controller 144 also includes a user input module 162 that is configured receive input signals from the other user input devices 152 and to generate and display images being displayed on the user input device 152. For example, the user input module 162 may retrieve image date being stored in the memory device 156 and transmit the image data to the user input device 152 to enable the display device to display the images to the caregiver. The user input module 162 also transmits signals to the state indicator 150 to operate the state indicator 150 to indicate the sensed position of the braking mechanism 62.

Figure 18:
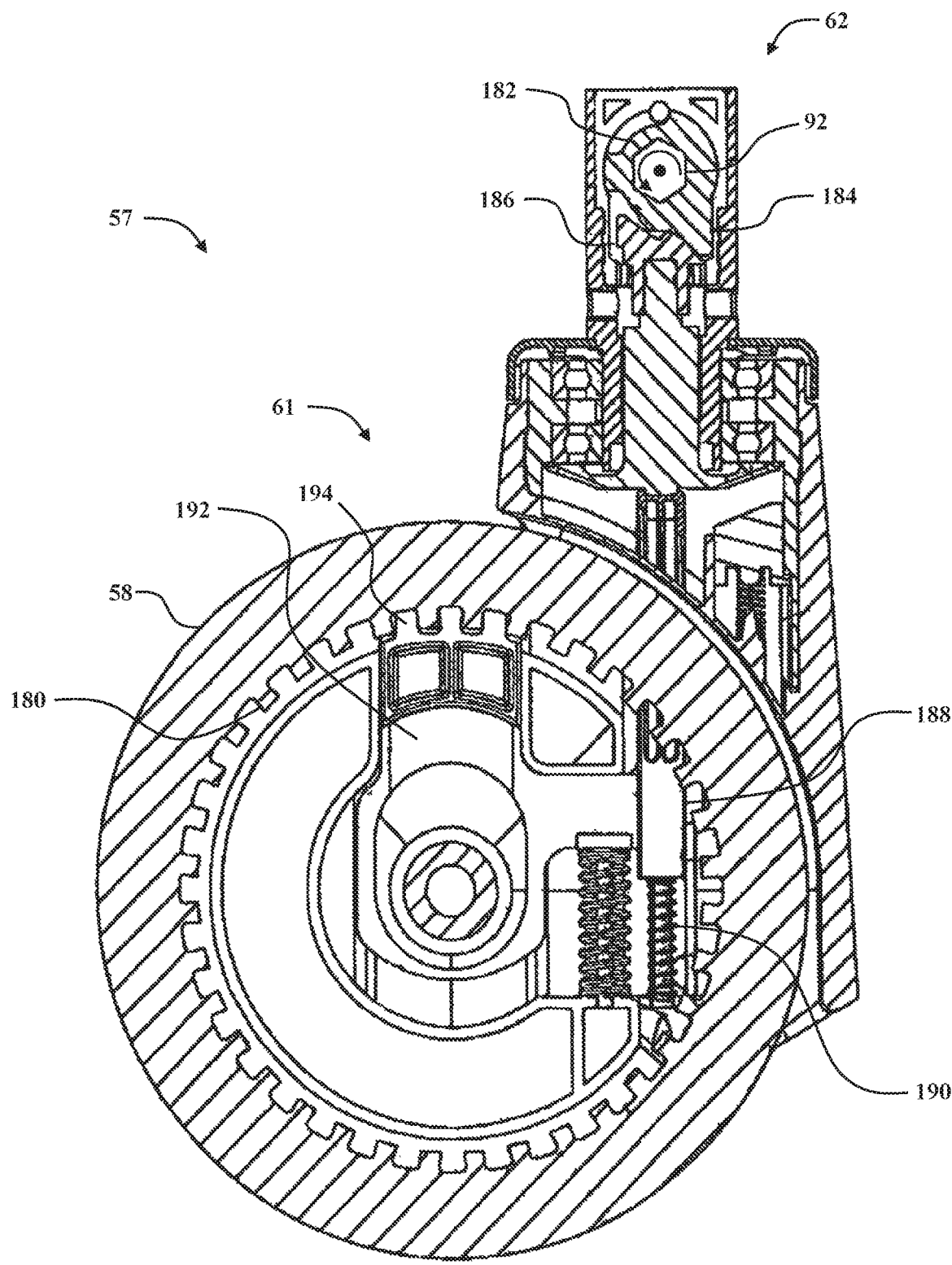
FIG. 18 is a schematic view of a braking mechanism that may be used with the electro-mechanical braking system with the braking mechanism in a braked state.
Figure 19:
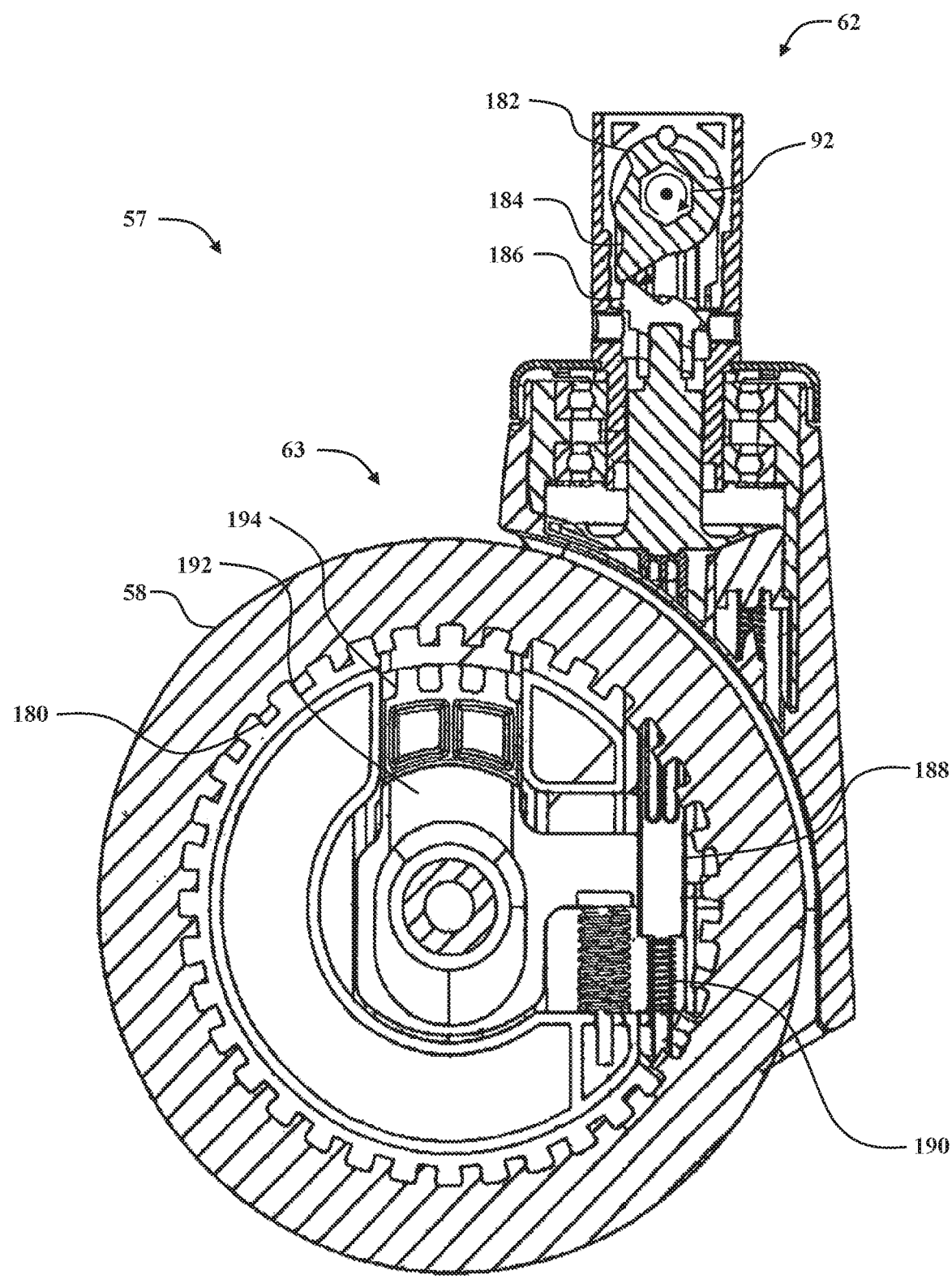
FIG. 19 is a schematic view of a braking mechanism that may be used with the electro-mechanical braking system with the braking mechanism in a released state.

Referring to FIGS. 18 and 19, in one embodiment, the wheel assembly 57 includes a plurality of teeth 180 defined along an interior surface of the wheel 58. The braking mechanism 62 includes an actuating eccentric member 182 that is coupled to the hex shaft 92. The actuating eccentric member 182 (also referred to as a cam) includes an actuating projection 184 that acts on a switching head 186. The switching head 186 is coupled to a switching pin 188 which is moveable in a vertical direction. A pressure spring 190 is attached to the switching pin 188 to bias the switching pin 188 in an upward vertical direction. A wheel braking member 192 is coupled to the switching pin 188 and includes a plurality of teeth 194 that are arranged to engage the teeth 180 defined along the interior surface of the wheel 58. During operation of the braking mechanism 62, as the hex shaft 92 is rotated, the actuating eccentric member 182 is rotated to move the actuating projection 184 along the switching head 186 to move the braking mechanism 62 between the braked state 61 (shown in FIG. 18) in which the wheel braking member 192 engages the teeth 180 defined along the interior surface of the wheel 58, and the released state 63 (shown in FIG. 19) in which the teeth 194 of the wheel braking member 192 are spaced a distance from the teeth 180 defined along the interior surface of the wheel 58.

During operation, when a caregiver wishes to engage or release the braking mechanism 62, the caregiver actuates one or more of the user input devices 152 (or the sensing device 146 may operate as a user input device). For instance, in the event the caregiver wishes to brake the wheels 58 to stop movement of the patient transport apparatus 30, the caregiver actuates the appropriate user input device 152. Upon actuation, the controller 144 sends output signals to the actuator assembly 100 to cause operation of the actuator assembly 100 to move the driving assembly 98 to the first position 122.

For example, as shown in FIG. 12, upon receiving a request to brake the wheels 58 from the caregiver via a user input device 152, the controller 144 operates the motor 126 to rotate the drive shaft 128 in the first rotational direction 130 to rotate the driving assembly 98 and move the positioning member 102 from the home position 125 to the first position 122. As the positioning member 102 moves from the home position 125 to the first position 122, the position member 102 contacts the driving actuation member 90 at an end of the travel path 114 and rotates the driving actuation member 90 in the first rotational direction 130. As a result, owing to the connection of the driving assembly 98 to the linkage assembly 66, the driving assembly 98, via the positioning member 102, moves the linkage assembly 66 along the first direction 72 to move the braking mechanism 62 to the braked state 61 (shown in FIG. 18) to brake the wheels 58. Once the driving assembly 98 has moved to the first position 120 and the braking mechanism 62 is in the braked state, the controller 144 sends an output signal to the actuator assembly 100 to return the driving assembly 98 to the home position 125 based on feedback from the sensor assembly 134. For example, the controller 144 operates the motor 126 to rotate the driving assembly 98 in the second rotational direction 132 to return the positioning member 102 to the home position 125. This enables the user to manually release the patient transport apparatus 30 using the manual actuator 68 without interference from the positioning member 102. In addition, the controller 144 transmits a signal to the state indicator 150 to operate the state indicator 150 to indicate the state of the braking mechanism 62 in the braked state.

Similarly, in the event the caregiver wishes to release the wheels 58 to enable movement of the patient transport apparatus 30, the caregiver actuates the appropriate user input device 152 (or the sensing device 146). Upon actuation, the controller 144 sends output signals to the actuator assembly 100 to cause operation of the actuator assembly 100 to move the driving assembly 98 to the second position 123. For example, as shown in FIG. 13, the controller 144 operates the motor 126 to rotate the drive shaft 128 in the second rotational direction 132 to rotate the driving assembly 98 and move the positioning member 102 from the home position 125 to the second position 123. As the positioning member 102 moves from the home position 125 to the second position 123, the position member 102 contacts the driving actuation member 90 at an opposite end of the travel path 114 and rotates the driving actuation member 90 in the second rotational direction 132. As a result, the driving assembly 98, via the positioning member 102, moves the linkage assembly 66 along the second direction 74 to move the braking mechanism 62 to the released state 63 (shown in FIG. 19) to release the braking mechanism 62 from the wheels 58. Once the driving assembly 98 has moved to the second position 122 and the braking mechanism 62 is in the released state, the controller sends an output signal to the actuator assembly 100 to return the driving assembly 98 to the home position based on feedback from the sensor assembly 134. For example, once the positioning member 102 has been moved to the second position 123, and the braking mechanism 62 is in the released state 63, the controller 144 operates the motor 126 to rotate the driving assembly 98 in the first rotational direction 130 to return the positioning member 102 to the home position 125. This enables the user to manually brake the patient transport apparatus 30 using the manual actuator 68 without interference from the positioning member 102. In addition, the controller 144 transmits a signal to the state indicator 150 to operate the state indicator 150 to indicate the state of the braking mechanism 62 in the released state.

In one embodiment, the caregiver may wish to operate the steer lock mechanism in the steer locked state in which one or more of the wheels 58 are prevented from swiveling. In the event the caregiver wishes to operate in the steer locked state, the caregiver actuates the appropriate user input device 152 (or the sensing device 142). Upon actuation, the controller 144 sends output signals to the actuator assembly 100 to cause operation of the actuator assembly 100 to move the driving assembly 98 to the third position 124. For example, as shown in FIG. 14, the controller 144 operates the motor 126 to rotate the drive shaft 128 in the second rotational direction 132 to rotate the driving assembly 98 and move the positioning member 102 from the home position 125 to the third position 124. As the positioning member 102 moves from the home position 125 to the third position 124, the position member 102 contacts the driving actuation member 90 at an end of the travel path 114 and rotates the driving actuation member 90 in the second rotational direction 132. As a result, the driving assembly 98 moves the linkage assembly 66 along the second direction 74 to move the steer lock mechanism to the steer locked state to prevent one or more wheels 58 from swiveling. Upon reaching the third position 124, the controller 144 transmits a signal to the state indicator 150 to operate the state indicator 150 to indicate the state of the steer lock mechanism in the steer locked state. After moving to the steer locked state, the actuator assembly 100 moves the driving assembly 98 to the home position 125, which enables the caregiver to manually release the steer lock mechanism or to manually brake the patient transport apparatus 30 using the manual actuator 68. For example, once the positioning member 102 has been moved to the third position 124, and the steer lock mechanism is in the steer locked state, the controller 144 operates the motor 126 to rotate the driving assembly 98 in the first rotational direction 130 to return the positioning member 102 to the home position 125.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient transport apparatus comprising:
   a support structure comprising a base and a patient support deck;
   a wheel assembly coupled to the base and comprising a wheel and a braking mechanism to brake the wheel;
   a linkage assembly coupled to the braking mechanism and arranged to place the braking mechanism in a braked state in which the braking mechanism brakes the wheel and a released state in which the braking mechanism is released from braking the wheel, the linkage assembly defining a positioning slot;
a manual actuator coupled to the linkage assembly to move the linkage assembly manually to place the braking mechanism in the braked state and the released state; and
an electrical braking assembly comprising:
a driving assembly coupled to the linkage assembly and comprising a positioning member disposed in the positioning slot, and
an actuator assembly coupled to the driving assembly and configured to move the driving assembly between a first position and a second position,
wherein a movement of the driving assembly to the first position causes the linkage assembly to place the braking mechanism in the braked state and a movement of the driving assembly to the second position causes the linkage assembly to place the braking mechanism in the released state, and
wherein the linkage assembly is arranged to move relative to the driving assembly to enable the braking mechanism to be manually actuated with the manual actuator.

2. The patient transport apparatus of claim 1, wherein the positioning slot provides a travel path for the positioning member, the travel path sized so that the positioning member is movable along the travel path from a center of the travel path to facilitate relative movement between the driving assembly and the braking mechanism to enable the braking mechanism to be manually actuated with the manual actuator.

3. The patient transport apparatus of claim 2, wherein the actuator assembly comprises a motor and a drive shaft rotatably coupled to the motor, the driving assembly coupled to the drive shaft such that a rotation of the drive shaft rotates the positioning member.

4. The patient transport apparatus of claim 3, wherein the driving assembly comprises a driving member coupled to the drive shaft, the positioning member extending from an outer surface of the driving member.

5. The patient transport apparatus of claim 4, wherein the linkage assembly comprises an actuation member rotatably coupled to the driving member, the actuation member comprising an outer surface having the positioning slot defined therethrough, the positioning member configured to contact an inner surface of the positioning slot to rotate the actuation member.

6. The patient transport apparatus of claim 5, wherein the linkage assembly comprises a link coupled to the actuation member and to the braking mechanism such that a rotation of the actuation member causes the link to operate the braking mechanism to place the braking mechanism in the braked state and the released state.

7. The patient transport apparatus of claim 6, wherein the actuation member comprises a sector gear, the link comprising an engagement slot configured to receive the sector gear therein and a plurality of engagement teeth configured to contact the sector gear with the sector gear positioned within the engagement slot.

8. The patient transport apparatus of claim 7, wherein the positioning slot comprises a length that is longer than a length of the positioning member such that the sector gear is freely rotatable with respect to the driving member to facilitate relative movement between the driving assembly and the braking mechanism to enable the braking mechanism to be manually actuated with the manual actuator.

9. The patient transport apparatus of claim 7, wherein the linkage assembly further comprises:
a second engagement slot defined through the link;
a second plurality of engagement teeth; and
a second sector gear positioned within the second engagement slot to contact the second plurality of engagement teeth; and
wherein the manual actuator comprises:
a shaft coupled to the second sector gear for rotating the second sector gear; and
a brake pedal coupled to the shaft to rotate the second sector gear to move the link when the brake pedal is manually actuated.

10. The patient transport apparatus of claim 9, wherein the linkage assembly further comprises:
a third engagement slot defined through the link;
a third plurality of engagement teeth; and
a third sector gear positioned within the third engagement slot to engage the third plurality of engagement teeth; and
wherein the wheel assembly comprises a hex shaft coupled to the braking mechanism and to the third sector gear such that a rotation of the third sector gear rotates the hex shaft to place the braking mechanism in the braked state and the released state.

11. The patient transport apparatus of claim 3, wherein the electrical braking assembly further comprises a sensor assembly configured to sense a position of the positioning member.

12. The patient transport apparatus of claim 11, wherein the actuator assembly is further configured to move the driving assembly to a home position between the first and second positions; and
wherein movement of the driving assembly to the home position allows the linkage assembly to move relative to the driving assembly to enable the braking mechanism to be manually actuated with the manual actuator.

13. The patient transport apparatus of claim 12, wherein the sensor assembly comprises:
a position indicator orientated with respect to the positioning member; and
a sensor arm configured to contact the position indicator with the positioning member in the home position.

14. The patient transport apparatus of claim 13, wherein the position indicator is coupled to the drive shaft such that a rotation of the drive shaft rotates the position indicator.

15. The patient transport apparatus of claim 3, wherein the electrical braking assembly comprises a torque limiting device operable between the motor and the positioning member to limit an amount of torque being applied to the positioning member by the motor.

16. The patient transport apparatus of claim 15, wherein the torque limiting device comprises one or more of a slip clutch, a spring loaded coupling, and a belt drive.

17. The patient transport apparatus of claim 1, further comprising:
a control assembly comprising:
a sensing device to sense a proximity of a user; and
a controller coupled to the sensing device and the electrical braking assembly, the controller configured to operate the electrical braking assembly upon receiving a signal from the sensing device indicating a sensed proximity of the user.

18. The patient transport apparatus of claim 17, wherein the control assembly further comprises:

a brake sensor coupled to the controller and configured to sense a position of the braking mechanism; and a state indicator coupled to the controller, wherein the controller is configured to operate the state indicator to indicate the sensed position of the braking mechanism.

19. The patient transport apparatus of claim 18, wherein the state indicator comprises one or more of a visual indicator, audible indicator, and tactile indicator to indicate the sensed position of the braking mechanism.

20. The patient transport apparatus of claim 18, wherein the manual actuator comprises a brake pedal, the state indicator and the sensing device being coupled to the brake pedal.

\* \* \* \* \*